US006536553B1

(12) United States Patent
Scanlon

(10) Patent No.: US 6,536,553 B1
(45) Date of Patent: Mar. 25, 2003

(54) METHOD AND APPARATUS USING ACOUSTIC SENSOR FOR SUB-SURFACE OBJECT DETECTION AND VISUALIZATION

(75) Inventor: Michael V. Scanlon, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/557,939

(22) Filed: Apr. 25, 2000

(51) Int. Cl.⁷ .......................... G01V 1/00; G01N 29/04
(52) U.S. Cl. .................. 181/108; 181/401; 73/636; 73/639; 367/178
(58) Field of Search .................. 73/639, 636, 594; 367/87, 97, 178; 181/108, 401

(56) References Cited

U.S. PATENT DOCUMENTS

| 4,174,636 A | * | 11/1979 | Pagano | 73/639 |
| 4,208,915 A | * | 6/1980 | Edwards | 73/639 |
| 4,285,243 A | * | 8/1981 | Collingwood | 73/639 |
| 5,802,013 A | * | 9/1998 | Earp | 367/178 |
| 6,131,695 A | * | 10/2000 | Earp | 181/108 |

* cited by examiner

Primary Examiner—Ian J. Lobo
(74) Attorney, Agent, or Firm—Paul S. Clohan, Jr.; William V. Adams

(57) ABSTRACT

An apparatus for detecting an underground abject includes a container in contact with the ground surface; a medium disposed in the container; at least one acoustic sensor disposed in the medium in the container; and an output device connected to the acoustic sensor. A portion of the container in contact with the ground is substantially acoustically transparent and conforms to contours of the ground. The acoustic impedance of the medium in the container is substantially the same as the acoustic impedance of the ground. A method of detecting an underground object includes receiveing reflected acoustic noise with at least one acoustic sensor immersed in a medium, the mediukm being desposed in a container in contact with a ground surface; converting the reflected acoustic noise to electrical signals; and, using an output device, converting teh eletrical signals to a form that can be sensed by a human to determine if the undergroung object has been detected.

21 Claims, 9 Drawing Sheets

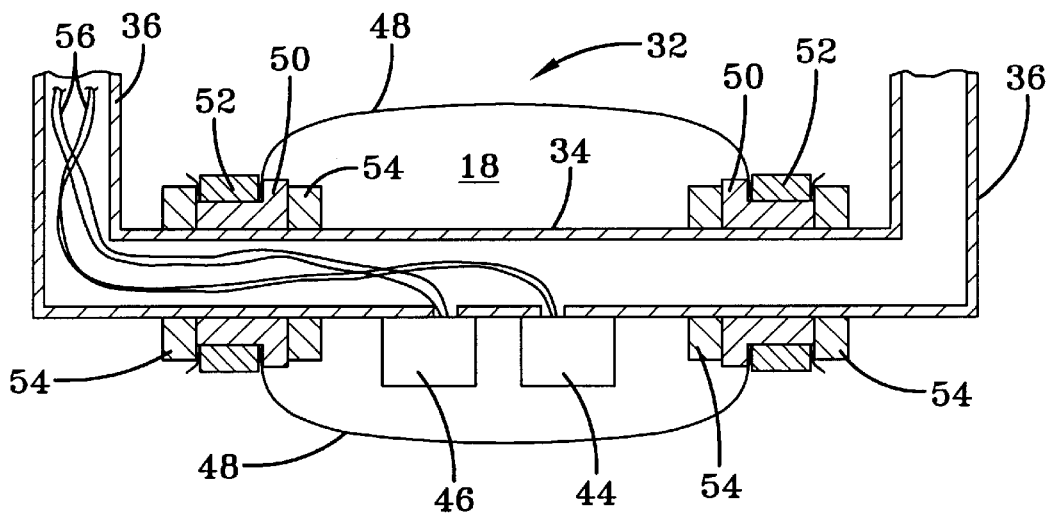
FIG-4
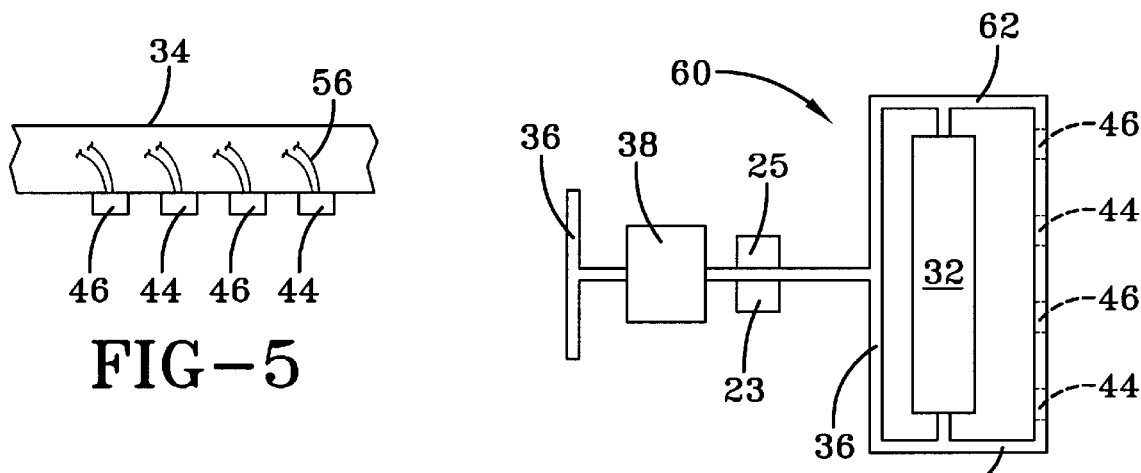
FIG-5
FIG-6
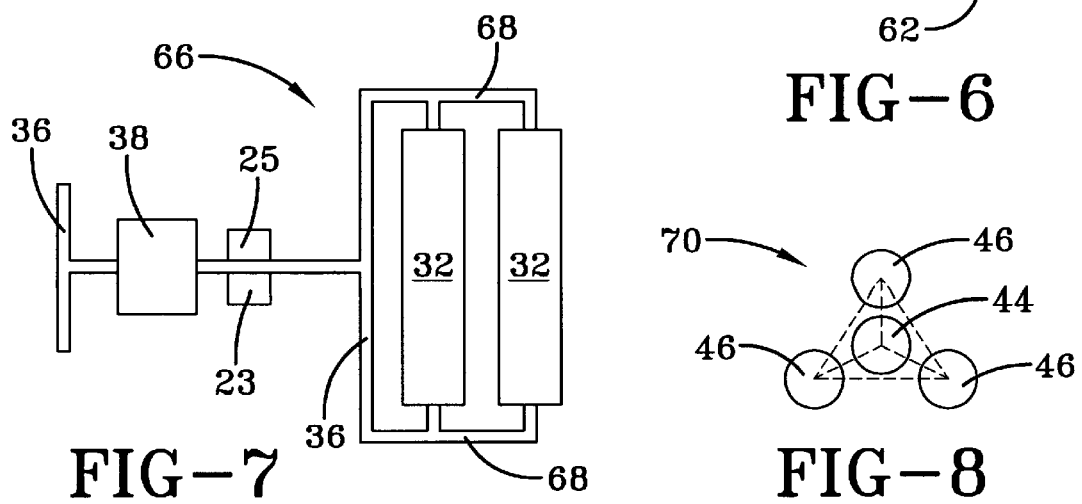
FIG-7
FIG-8

METHOD AND APPARATUS USING ACOUSTIC SENSOR FOR SUB-SURFACE OBJECT DETECTION AND VISUALIZATION

STATEMENT OF GOVERNMENT INTEREST

The invention described herein may be manufactured and used by or for the Government of the United States of America for government purposes without the payment of any royalties therefor.

BACKGROUND OF THE INVENTION

The invention relates in general to acoustic sensors and in particular to the use of acoustic sensors to identify underground objects.

More than 100 million landmines have been deployed throughout the world, resulting in tens of thousands of people dead or maimed every year. U.S. soldiers are deeply immersed in peacekeeping, humanitarian, and military operations in areas of the world cluttered with mines. There are diverse technologies for detecting mines and explosive ordnance with varying degrees of performance, cost, and practicality.

Magnetometers are used to detect ferromagnetic objects such as mines. However, many mines are made of plastic with minimal metal components, and metallic debris often confounds magnetometer detections. The use of thermal imaging for mine detection relies on the mine releasing or storing thermal energy at different rates than its surrounding. Explosive vapor sensors are effective, but are big and slow. Thermal neutron activation for bulk explosive detection has practical limits. X-ray backscatter, mm-wave emissivity, chemical/biosensors, ultra-wide and mm-wave radars are also promising (See Gros & Bruschini, Int'l Symp. on Meas. & Control in Robotics, Brussels, May 1996).

Ground penetrating radar emits electromagnetic waves and monitors the reflections from the soil caused by dielectric variations from underground objects. However, nonmetallic mines are only detectable if their dielectric properties strongly contrast with their surrounding. Target-specific resonances can be present in the reflected signal (See Peters, Daniels, Young, "Ground Penetrating Radar as Subsurface Environmental Sensing Tools" Proc. IEEE, Vol. 82, No. 12, December. 1994, pp. 1802–1822).

Seismic sensors can also detect resonances for discrimination between metal, plastic, wood, and rocks. Seismic echo-rangers observe mine echoes via generation and detection of scattered Rayleigh and/or surface compressional waves reflecting off a buried mine and returning to a sensor array (See BBN Systems and Technologies Corp., "Feasibility of Acoustic Landmine Detection: Final Technical Report," Report No. BBN-TR-7677, May 19, 1992).

Acoustic (ultrasonic) imagery is commonplace in medicine. Broadband acoustic detection is effectively employed in underwater warfare and the detection of underwater mines buried in sea-bottom silt. Reflections at material discontinuities, as well as mine dimension, shape, materials, and depth contribute to the distortion of the induced and resultant sound field. These effects, often subtle modifications to amplitude, phase, and frequency, are easily monitored to extract information relating to an object within its surroundings.

Acoustic systems are capable of good penetration through very wet and heavy ground, such as clay, "but are likely to experience problems at the air-ground interface." (See Bruschini & Gros, "A survey of Current Sensor Technology Research for the Detection of Landmines," Int'l Workshop on Sustainable Humanitarian Demining (SusDem'97), Sep. 29 –Oct. 1, 1997 Zagreb, Croatia). Successful imaging with 15 MHz was conducted on a mine submerged slightly underwater, like deployed in rice fields. Such high frequencies will not normally penetrate the ground, and more appropriate frequencies and coupling should be used. Transmitting 3 kHz pulse bursts into the ground has permitted detecting objects down to 12 inches, and shown that rock-reflected signals exhibit irregular axes of reflections (See Morita. "Land Mine Detection System," TRW Final Report AT-73-2, Feb. 23, 1973).

The introduction of soliton-like shock waves into the ground showed they had weak interaction with the ground, which causes minimal dispersion, and can provide much information from mine reflected energy (See Sen, Physical Review Letters, vol. 74, p. 2686–2689, 1995 and Physical Review E, vol. 54, pp. 6857–6865, 1996). Millisecond acoustic burst/impulse techniques provide advantages over continuous wave (CW) techniques. Return pulse gating allows interpretation of travel path and spectral modifications, since the pulse contains typically 200 Hz to 20 kHz data (See Rogers and Don, "Location of Buried Objects by and Acoustic Impulse Technique," Acoustics Australia 22 5–9, 1994). A significant problem lies in isolating small object pulses from other, often dominant, signals, and coping with ground contours and irregularities (See Don, "Using Acoustic Impulses to Identify a Buried nonmetallic Object," Abstract 2aPA3, 127th Meeting of the Acoustical Society of America, May 1994). CW and broad-band acoustics may impart more energy to better induce structure resonances.

A US Army study found that disturbed soil covering a mine absorbed acoustic energy while the surrounding undisturbed soil reflected the acoustic energy. Where the acoustic energy was absorbed, the ground vibrated at seismic frequencies that depended on the acoustic input, soil properties, and on the mine (See More, Dilworth, Lewis, Wesolowicz, and Stanich, "Acoustic Mine Detection," Daedalus Enterprises Final Report, Feb. 7, 1990). This implies that complementary sensor technologies, such as passive/active acoustic/seismic can enhance detection and identification through sensor fusion.

The present invention employs acoustic array techniques to localize buried objects and interpret the landmine's environment. One embodiment of the present invention is a low-cost, hand-held mine detector that rolls or slides across the ground, suitable for a soldier to inspect and clear, for example, a two-foot wide path for him to walk. In some embodiments, the invention incorporates data from seismic and electromagnetic sensors to enhance detection and reduce false alarms. Acoustic coupling and imaging can also aid in the nondestructive evaluation of materials and structures.

SUMMARY OF THE INVENTION

In accordance with the invention an apparatus for detecting an underground object comprises a container in contact with a ground surface; a medium disposed in the container; at least one acoustic sensor disposed in the medium in the container, for detecting acoustic noise; and an output device connected to the acoustic sensor. The apparatus further comprises at least one acoustic source that emits acoustic noise. The medium is at least one of liquid and gel. At least a portion of the container that contacts the ground surface is substantially acoustically transparent. The at least one acoustic source may be disposed in the medium in the container.

The portion of the container that contacts the ground surface is made of a substantially flexible material such that the portion of the container that contacts the ground surface substantially conforms to a contour of the ground surface. The substantially flexible material is one of rubber, polyethylene, polyvinylchloride, vinyl and a plastic material. The medium is one of water, oil and oil well drilling mud. The output device comprises a visual display, an auditory device or a tactile device.

In one embodiment the container is a roller having a generally cylindrical shape, the roller including a shaft that passes through the roller wherein the at least one acoustic sensor is mounted on the shaft. At least one acoustic source that emits acoustic noise may also be mounted on the shaft. A handle may be attached to the shaft for moving the roller across the ground surface. The acoustic noise is one of swept sine impulsive, broadband and continuous wave.

Preferably, an acoustic impedance of the medium is substantially the same as an acoustic impedance of material around the underground object.

The apparatus may further comprise a data processor connected between the at least one acoustic sensor and the output device. The data processor compares data from the at least one acoustic sensor and the at least one acoustic source. The data are compared for variations in at least one of phase, amplitude, frequency, time of arrival and echoes.

The apparatus may further comprise a rear wheel assembly attached to the handle, for decreasing loading of the roller on the ground surface.

In one embodiment, the apparatus further comprises a calibration bar including a reflective surface, the reflective surface being suspended beneath the at least one acoustic sensor and the at least one acoustic source for calibrating the at least one acoustic sensor and the at least one acoustic source.

In a preferred embodiment, the apparatus further comprises a collection chamber assembly mounted on the shaft inside the roller at one end thereof, the collection chamber assembly comprising a chamber with openings formed therein for collecting and releasing higher density medium.

The shaft may include a bearing portion and a shroud portion, the at least one acoustic sensor and the at least one acoustic source being mounted on the shroud portion. An acoustic absorber may be mounted on a top of the shroud portion.

In another embodiment, the shaft includes a transverse portion and at least one longitudinal portion, the at least one longitudinal portion being substantially parallel to a direction of movement of the roller the at least one acoustic sensor and the at least one acoustic source being mounted on the at least one longitudinal portion.

In a preferred embodiment, the container comprises a rigid top plate, the at least one acoustic sensor being mounted on a bottom of the rigid top plate.

In another embodiment, the apparatus comprises a plurality of rollers, the plurality of rollers comprising two end rollers and at least one interior roller; a transverse member; two end arms connected at one end to an end roller and at the other end rigidly connected to the transverse member; at least one rocker arm connected at one end to the at least one interior roller and at the other end rotatably connected to the transverse member; and a handle connected to the transverse member.

The apparatus may further comprise a global positioning system attached to the apparatus.

In another embodiment the container is a roller having a generally cylindrical shape, the roller including two end caps, a support structure mounted between the two end caps, at least one mounting plate attached to the support structure for receiving the at least one acoustic sensor, a pair of shaft hubs attached to external surfaces of the end caps and a transmitter attached to one of the pair of shaft hubs.

The invention further provides an apparatus for inspecting a pipe comprising at least one generally cylindrical roller having a substantially acoustically transparent portion that contacts an interior of the pipe; a shaft that passes through the at least one generally cylindrical roller; at least one acoustic sensor mounted on the shaft; a medium contained in the roller, the at least one acoustic sensor being immersed in the medium, the medium having an acoustic impedance substantially the same as an acoustic impedance of the pipe; a central support arm and a central support ring rigidly connected to the central support arm; a pair of roller support arms connected at first ends to ends of the roller shaft and at second ends pivotally connected to the central support ring; a pair of expansion springs connected at first ends to the central support arms and at second ends to the pair of roller support arms, respectively, wherein the expansion springs force the roller against the interior of the pipe; one of a radio transmitter and a data logger mounted on the central support arm and connected to the at least one acoustic sensor; and means for moving the at least one roller through the pipe.

Another aspect of the invention is a method of detecting an underground object comprising receiving at least one of acoustic noise emanating from and acoustic noise reflected from the underground object with at least one acoustic sensor immersed in a medium, the medium being disposed in a container in contact with a ground surface; converting the received acoustic noise to electrical signals; using an output device, converting the electrical signals to a form that can be sensed by a human to determine if the underground object has been detected. A portion of the container in contact with the ground surface is substantially acoustically transparent. An acoustic impedance of the medium is substantially the same as an acoustic impedance of material around the underground object.

The method further comprises conforming the portion of the container in contact with the ground surface to contours of the ground surface. The method further comprises processing the electrical signals with a data processor.

In one embodiment, the method further comprises converting the electrical signals to the form of one of a visual display, auditory cue and tactile cue.

Another aspect of the invention is an apparatus for analyzing a material comprising a container in contact with a surface of the material; a medium disposed in the container; at least one acoustic sensor disposed in the medium in the container, for detecting acoustic noise; and an output device connected to the acoustic sensor. The apparatus further comprises at least one acoustic source that emits acoustic noise.

Yet another aspect of the invention is a method of analyzing a material comprising receiving acoustic noise from the material with at least one acoustic sensor immersed in a medium, the medium being disposed in a container in contact with a surface of the material; converting the acoustic noise to electrical signals; using an output device, converting the electrical signals to a form that can be sensed by a human.

In one embodiment, the material is soil and the method further comprises analyzing the soil for at least one of soundspeed, porosity, density and water content.

Further objects, features and advantages of the invention will become apparent from the following detailed description taken in conjunction with the following drawing.

BRIEF DESCRIPTION OF THE DRAWINGS

Throughout the Figures, reference numerals that are the same refer to the same features.

FIG. 4 is an enlarged, cutaway schematic view of the container of the embodiment of FIGS. 2 and 3.

FIG. 5 is a schematic partial view of an embodiment with multiple sources and sensors.

FIG. 6 is a schematic top view of an embodiment with multiple sources and sensors located outside of the container.

FIG. 7 is a schematic top view of an embodiment having two containers.

FIG. 8 schematically shows a triad arrangement of sensors.

DETAILED DESCRIPTION OF THE PREFERRED EMBODIMENTS

Throughout the specification and claims of the instant patent application, the word "ground surface" means the ordinary dictionary meaning and, in addition, includes, but is not limited to, the upper layer of the earth, asphalt, concrete, any material laid over the surface of the earth, and floors, walls and roofs of structures. "Underground" means the area underlying the "ground surface," as defined above. "Object" means the ordinary dictionary meaning and, in addition, includes, but is not limited to discontinuities, voids, material properties and dimensions.

Figure 1:
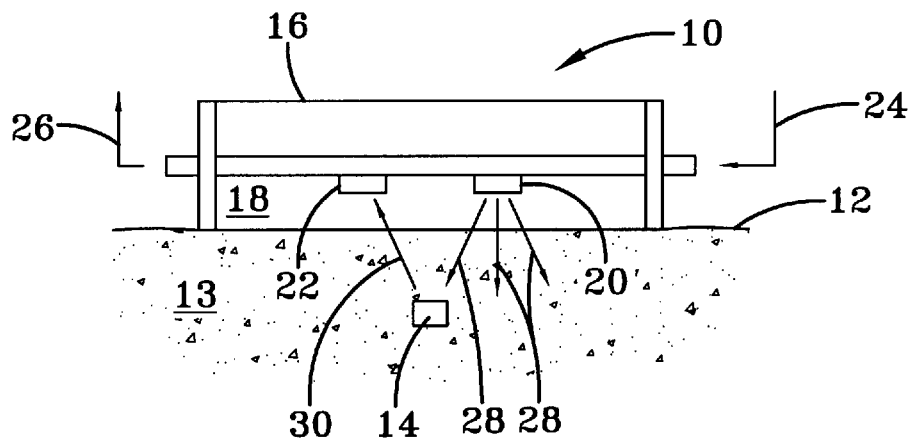
FIG. 1 schematically illustrates the general principle of operation of the invention.

FIG. 1 schematically illustrates the general principle of operation of the invention. An apparatus 10 for detecting an underground object 14 includes a container 16 in contact with the ground surface 12. A medium 18 is disposed in the container 16. At least one acoustic sensor 22 is disposed in the medium 18 in the container 16. The acoustic sensor 22 detects acoustic noise represented by arrow 30 that is reflected by the underground object 14. Arrow 26 represents the output signal from the acoustic sensor 22. Ambient conditions in the vicinity of the object 14 may include acoustic noise. Alternatively, or in addition to ambient acoustic noise, acoustic noise represented by arrows 28 may be emitted by at least one acoustic source 20 toward the underground object 14. Arrow 24 represents input signals to the acoustic source 20.

In general, the acoustic sensor 22 is placed in fluid communication with the ground 13 through a medium 18 (coupling material) such as water, or other dense liquid. The product of soundspeed and density is termed the acoustic impedance, and when two bodies have similar acoustic impedances, sounds will travel between them with minimal, if any, losses. The medium 18 is contained in a substantially flexible container or bladder 16 in the shape of a cylinder, for example. The shape of the container 16 may be varied depending on the particular application or sensor array geometry.

At least a portion of the container 16 that contacts the ground surface 12 is substantially acoustically transparent. Very thin material, such as rubber, PVC, vinyl, polyethylene, and other plastics are substantially acoustically transparent when sandwiched between the medium 18 and the ground surface 12. The sensor 22 remains in an essentially fixed linear geometry hovering over the ground surface 12 to facilitate beamforming while eliminating the huge losses associated with coupling airborne sounds to the ground. The medium 18 acts as a sound conduit through the container 16 and facilitates receiving low-level returning signals that would have otherwise undergone large attenuations resulting from sounds radiating from the ground to the air.

Puncture and tear resistance is also an important consideration for the portion of the container 16 that contacts the ground. The container 16 and the contained medium 18 deform to the contours of the ground surface 12. The ground surface 12 may be normal ground with sticks, grass, and rocks, or pavement. For the purposes of landmine detection, the soil-loading resulting from the apparatus 10 cannot be high enough to detonate a pressure sensitive mine. The container 16 will deform around sticks, rocks, or even surface landmines. Density and hardness gradients between these surface objects and the container 16 will generate a return, and will permit imaging or detection of surface objects, surface contour, and buried objects. A homogeneous material, such as sand, would be an easier environment to interpret the returns than that of a non-homogeneous material, such as soil, where the embedded debris, rocks, sticks, organic material, roots, or trash can produce many confusing returns. These returns add complexity to the detection and visualization computations.

In one embodiment, a plurality of acoustic sensors 22 are disposed in the medium 18. The medium 18 and container 16 deform to the contours of the ground surface 12. The medium 18 and container 16 have an acoustic impedance comparable to that of the ground 13 to facilitate energy transfer and eliminate losses at the air-ground interface. Continuous wave, broadband and impulsive acoustic array techniques are used to localize the buried object 14 and interpret the buried object's surrounding.

Some important applications of the invention are for landmine or buried pipe detection. One embodiment of the invention is a low-cost, hand-held mine detector that rolls or slides across the ground, suitable for a person to inspect and clear, for example, a two-foot wide path. Other airborne acoustic detection systems are very likely to experience significant acoustic transmission losses at the air-ground interface. However, to lessen these losses, the present invention includes a unique medium-filled container 16 with conformal walls to enhance the coupling to the ground 13.

The acoustic sources 20 send out various acoustic waveforms 28. The sensors 22 detect the returning echoes and emissions 30 to determine if an object 14 buried below the surface 12 has affected the acoustic waveform 28. The reflections 30 of the incident wave 28 return to the surface and are detected at varying times by several of the sensors 22 within the array. These time differences are useful for determining distance from the object 14 to the sensor 22, radii of curvatures, and multipath. How the waveforms are different with respect to other sensors helps determine proximity and object properties.

The medium 18 in the container 16 is specially chosen to have similar sound speed and density to the material of the ground 13 and helps to match the acoustic impedance of the sensor 20 to the ground 13 that contains a mine or other object 14. Sounds within one material prefer to travel into one with similar properties. Acoustic impedance is the quality that determines how much acoustic energy will travel from one material into another. Mismatches create reflections and losses. Snell's law is applicable when impedances are matched. Ray theory is simplified by eliminating the refraction caused by diverse sound speed and density.

The medium 18 preferably has properties that match as close as possible the densities and sound speeds of the ground 13 that is below the container 16. A typical velocity of sound in soil is on the order of 500 m/s. Soil densities vary depending on composition, but typically range between the following: clay: 1460 kg/m3, sand: 1515 kg/m3, soil: 2050 kg/m3, rock: 2150–2680 kg/m3, wood: 420–640 kg/m3. Water content of the ground can also vary the properties. A typical landmine environment may be similar to the following:

| Location | Sand | Clay | |
|---|---|---|---|
| Yuma Proving Grounds, NM | 86% | 6% | Water content ~ 0–20% |
| Eglin AFB, FL | 94% | 2% | |

It should be noted that a liquid is not necessarily the only alternative for the medium 18. Gels (liquid or solid) and solids with complementary transmission properties to the ground 13 may be used as the coupling medium 18. One advantage of using a liquid is that variations in the ground contours will be overcome by the liquid's ability to conform to these contour variations due to gravity and the liquid's ability to seek its lowest level. Gel materials, such as silicone, may deform somewhat, but will not give absolute liquidity like a liquid will. Any liquid may be used, some will perform better than others. Oil and water are two choices for liquids for medium 18. Because the density of dirt, rock, clay, and sand is so much more than air, significant losses occur when sounds travel from the air into the ground, as well as when sounds reflect off an object buried under the ground and reradiate into the air.

A liquid and particulate mixture, such as "mud" used in oil well drilling, is another choice for medium 18. These mixtures are very dense, and the particulate is fine enough to remain in suspension a long time. The mud pulsing industry (drilling of oil wells) uses a slurry called "mud" which has very fine particulate suspended in a liquid to bring the well-boring debris to the surface. Drilling mud is denser than the ground. When introduced near the drilling head deep inside the bored hole, the mud settles to the bottom and forces the less dense debris to the top of the liquid column, and ultimately up the outside of the boring shaft to the surface.

Drilling mud would be a good medium for sound coupling. It is very dense and essentially homogeneous. Mud for drilling can be weighted up with Barite to give densities of 8.4 to 15.3 pounds per gallon (1006–1832 kg/meter cubed). Water and bentonite are used to add/build viscosity, and barite is used to build weight. The piezo ceramic sensors 22 and sources 20, encased in a rubber protective shield if necessary, would be directly in contact with the mud.

Other additives can be used with any liquid to create the proper acoustic impedance to match the container 16 to the ground 13. Depending on the ground type, different liquids can be used inside the container 16 to match the acoustic impedance between the container and whatever the ground type happens to be at that location. The container 16 is preferably a self-contained and sealed liquid system, but the density characteristics could be varied when needed.

Echolocation, synthetic aperture radar (SAR), side-scan-sonar, and towed array techniques are directly applicable to the invention. Reflections at material discontinuities, as well as mine shape, materials, and depth contribute to the variations of the induced and resultant sound field. These effects are often subtle modifications to amplitude, phase, and frequency, and can be exploited to extract information relating to an object within its surroundings.

Figure 2:
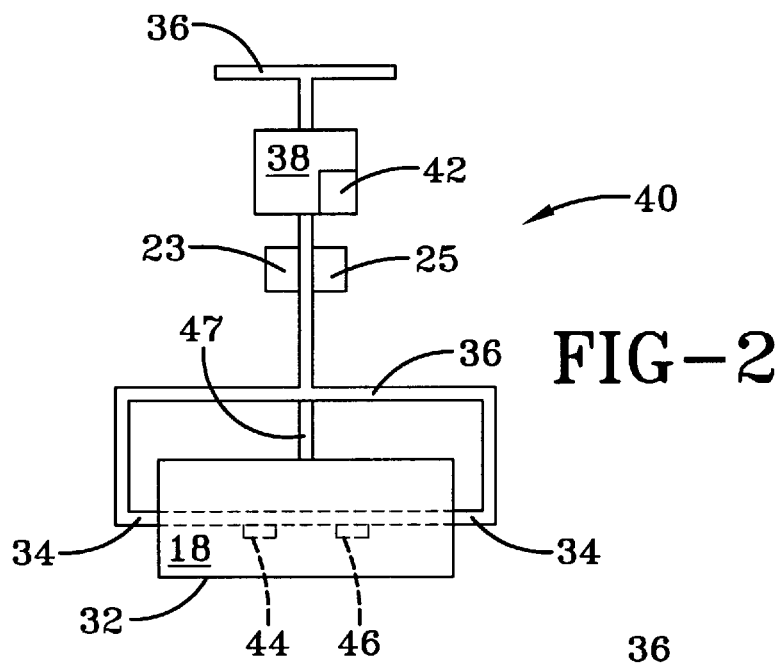
FIG. 2 is a schematic front view of an embodiment of the invention.
Figure 3:
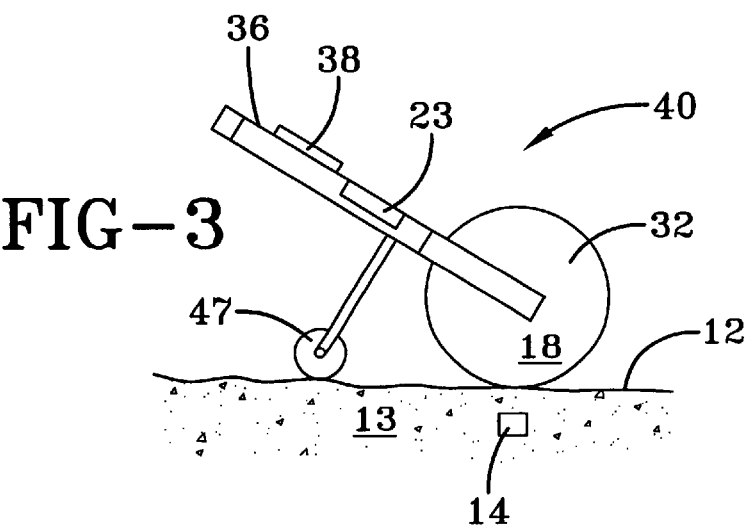
FIG. 3 is a schematic side view of the embodiment of FIG. 2.

FIG. 2 is a schematic front view of an embodiment of the invention. FIG. 3 is a schematic side view of the embodiment of FIG. 2. Referring to FIGS. 2 and 3, an apparatus 40 for detecting an underground object 14 includes a generally cylindrical container or roller 32, a medium 18 disposed in the roller 32, a shaft 34 that passes through the roller 32 and a handle 36 attached to the shaft 34. An acoustic source 44 that emits acoustic noise toward the underground object 14 is mounted on the shaft 34. An acoustic sensor 46 that detects acoustic noise reflected by the object 14 is also mounted on the shaft 34. The shaft 34 and handle 36 are preferably hollow so that the electrical wiring to the source 44 and sensor 46 may be disposed therein. The shaft 34 and handle 36 may be made of a rigid metal or plastic material. Shaft 34 may be generally cylindrical or may be formed in other shapes and configurations.

Acoustic source 44 includes acoustic source electronics 23. Acoustic source electronics 23 includes, for example, a power supply and a signal generator. Details of the acoustic source electronics are within the knowledge of one of ordinary skill in the art and will not be discussed in further detail. Acoustic sensor 46 includes acoustic sensor electronics 25. Acoustic sensor electronics 25 includes, for example, a preamplifier. Details of the acoustic sensor electronics are within the knowledge of one of ordinary skill in the art and will not be discussed in further detail. Both the acoustic source electronics 23 and acoustic sensor electronics 25 are preferably mounted on handle 36.

The apparatus 40 also includes an output device 38, preferably mounted on the handle 36. The output device 38 is electrically connected to the sensor 46. The output device 38 provides an indication of the detection of the object 14. The output device may provide a visual or auditory response to a detection of the object 14. For example, the output device may be a lighted display, such as an LED, or a set of headphones to be worn by a person operating the apparatus 40. Preferably, the output device 38 also includes a data processor (microprocessor or computer) 42 to process signals from the sensor 46. The source 44 may also be electrically connected to the data processor 42 for comparison of the signal generated by the source 44 with the signal received by the sensor 46. Display of the resulting data and detections can be in the form of visual indicators (light arrays, computer screens, remote monitors, or heads-up displays), audio indicators, tactile feedback, or control a ground marking method such as paint or chemical marker to indicate the location of a suspected object.

To reduce the load of the roller 32 on the ground surface 12, the output device 38 including data processor 42 and acoustic source and sensor electronics 23, 25 may be carried by the operator rather than mounted on the handle 36. Another way to reduce ground loading by the roller 32 is to include a rear-wheel assembly 47 that transfers some of the load toward the rear. In general, a loading maximum of three pounds per square inch is a maximum loading for typical anti-personnel mines. The tolerable loading for anti-tank mines is much higher.

FIG. 4 is an enlarged, cutaway schematic view of the roller 32 of the embodiment of FIGS. 2 and 3. The roller 32 includes a substantially acoustically transparent portion 48. The portion 48 is made of the same material as the acoustically transparent portion of the container 16 discussed above with reference to FIG. 1. A medium 18 is disposed in the roller 32. The source 44 and sensor 46 are immersed in the medium 18. The composition and properties of the medium 18 are as discussed above with regard to the medium 18 of FIG. 1. The substantially acoustically transparent portion 48 is similar to a "bag" or "bladder" and will hereinafter be referred to as the bladder 48.

Bearings 50 are fitted on each end of shaft 34. The bearings 50 are free to rotate around non-rotating shaft 34. The ends of bladder 48 are clamped to the surface of bearings 50 by, for example, hose clamps 52. Inner and outer bearing seals 54 are tightly fitted to the non-rotating shaft 34. Electrical wiring 56 connects the sensor 46 and source 44 to the output device 38. The wiring 56 is disposed in the interior of the shaft 34 and handle 36. The interior of the shaft 34 and handle 36 may be filled with air or an electrically insulating material.

As the operator pushes on the upper part of the handle 36 and the apparatus 40 moves forward, friction between the bladder 48 and the ground surface forces the bladder 48 and bearings 50 to rotate around the shaft 34. The orientation of the source 44, sensor 46 and shaft 34 is fixed and non-rotating. The bladder 48 and medium 18 rotate around the shaft 34. The source 44 and sensor 46 orientation with respect to the ground is preferably not changing, and maintains the same directional sensitivity. However, omni- and uni-directional sensors 46 and sources 44 can be used to provide selectable directivity. Although the preferred method of use is a hand-held device that is pushed by a person, the same device could be attached to a vehicle or robot and moved with the platform. Larger length arrays may be used to clear roads or large sections of beaches. Inspection arrays can be used in yards, construction zones, or other areas where underground visualization is necessary.

FIG. 5 is a schematic partial view of shaft 34 with multiple sources 44 and sensors 46. The sources 44 and sensors 46 are attached to shaft 34. Wiring 56 from each source and sensor is routed through the shaft 34 to the handle 36.

FIG. 6 is a schematic top view of an embodiment 60 with multiple sources 44 and/or multiple sensors 46 located outside of the roller 32. Apparatus 60 is similar to apparatus 40 except that a frame 62 is attached to the shaft 34 or, alternatively, to the handle 36. Frame 62 may be made of the same material as shaft 34 and handle 36. Sources 44 and sensors 46 are mounted on frame 62. It should be understood that frame 62 may include only additional sources 44, only additional sensors 46 or a combination of additional sources 44 and sensors 46. The wiring for the additional sources and sensors is routed through the interior of frame 62 to handle 36. The additional sources and/or sensors may also be mounted on a frame (not shown) that extends behind or to the side of roller 32.

Location of the sound sources 44 may be combined to impart as much acoustic energy into the ground as possible. The amplitude and type of sound emitted, such as impulsive, broadband, or continuous wave, may be modified based on the soil type and type of object to be detected. Generally, the louder and more impulsive the noise source the better. Sound sources 44 may even be in contact with the ground near the roller 32. The benefit of suspending the sources above the ground is that they could not detonate a pressure sensitive mine.

A disadvantage of suspending the sources 44 above the ground is that very high amplitudes are necessary to overcome atmospheric propagation losses and coupling mismatches in order to achieve high amplitude mechanical waves within the inspection area medium, such as sand or soil. Numerous sound sources 44, either in the roller 32 or suspended above the ground, can be activated simultaneously or independently in a synchronous order. The rate of sequential emitter activation would be determined by sensor and source spacing, anticipated depth of objects to be detected and propagation distances.

Liquid coupled and air-coupled sensors 46 may be combined to extract dissimilar indications relating to the same object. Combining source 44 and sensor 46 combinations within a single roller 32 in conjunction with airborne acoustic detection sensors 46 suspended over the ground (see FIG. 6) provides useful data for fusion and correlation. For example, the radius of curvature and signal strength of outgoing and incoming waveforms can be monitored at the sound-originating roller 32, as well as simultaneously comparing this data to the ground-to-air radiant energy resulting from reflections off the object as detected by air borne acoustic sensors 46.

Embodiment 60 of FIG. 6 allows forward observation without contacting the ground. Therefore, the ground contacting roller 32 can stop short of a buried object. Of course, if ground contact over/on the object is acceptable, a second roller 32 could be located in front of the first roller 32, in lieu of the air borne sensors 46 and sources 44. FIG. 7 is a schematic top view of an embodiment 66 wherein a second roller 32 is disposed in front of the first roller. It should be understood that the second roller 32 may include only sources 44, only sensors 46 or both sources and sensors. The front roller 32 is connected to the shaft 34 or handle 36 by a frame 68. Frame 68 may be made of the same material as shaft 34 and handle 36. The front and rear rollers 32 can alternately send and receive acoustic waveforms for timing, shadowing, multipath, and other propagation effects.

The sounds emitted by source(s) 44 for the purposes of underground investigation can be impulsive signals repeated at regular or varying intervals, broadband noise with varying bandwidths and amplitude relationships, pseudo and random noise, swept sine waves, ramps, or continuous wave signals such as tonals. Acoustic noise sources 44 comprise numerous piezoelectric, polyvinyldineflouride (PVDF), solenoid, magnetic armature, explosive, electro-dynamic, electrochemical, electromagnetic, electromechanical, radio frequency (RF) or laser induced mechanical waves that create propagating waves detectable by the sensor(s) 46. An advantage of using a piezoelectric element is that it can be used as either a sound sensor or a sound source by either monitoring resultant voltage or applying a voltage, respectively. High amplitude source waveforms can be created with explosives, such as a firecracker or propane cannon, or spark gap generators. Mechanical devices can create the high amplitude waveforms required. Spring or solenoid activated impacts can produce high amplitude and high bandwidth signals.

Acoustic sensors 46 can include piezoelectric, magnetorestrictive, PVDF, magnetic armature, laser or RF Doppler velocimetry, fiber-optic, fluidic, accelerometer, or any other method to transduce pressure or movement propagating in soil or fluid media.

Various forms of mechanical waves in and within the soil molecules (seismic, acoustic, and actual macroscopic ground displacement) can be observed and measured with the acoustic sensor(s) 46. Mechanical waves traveling through the ground will be reflected off buried objects, or induce resonances resulting from mechanical stimulation that will also emanate from the object, and be detected by the acoustic sensor 46. An impulsive signal by definition contains all frequencies, and can excite a resonance in a mine-like structure that may contain various materials or voids. The advantage of using impulse sources can be seen in the approach and retreat from a target, and the resulting phase shift (Doppler) associated with the relative approach or retreat from a target of interest.

Complex resonances result from non-homogeneous structures, such as a plastic mine casing that contains explosive materials and a metallic detonator with air voids. This non-homogeneity creates a characteristic structure borne resonance that can be indicative of the type or class of mines being observed, and acoustic sensors can be optimized to characterize these resonant properties. These resonances also help distinguish plastic or metal mines from clutter, such as rocks, roots, and other buried objects.

Signal processing techniques include higher order spectral features, Weiner filters, matched filters, thresholding, normalization, noise reduction, adaptive filters, and other feature extraction techniques such as Wavelets, auto- and cross-correlation techniques, and Fourier techniques. Dual-spectrum synthetic-aperture sonar techniques may provide different capabilities for detailed resolution and ground penetration. Use of principle component analysis or harmonic line analysis to choose most prominent spectral features of object below array. The most dramatic frequency change from one location to another will be indicative of an object buried below the surface. An average of all the sensors will provide an "average background" for comparison purposes. Another method of averaging data is to take subsequent lineal measurements from the same sensor, and have a running average with which successive measurements are compare to. Obviously, a combination of inter-sensor and geographic data can be used for a more global average. Combining more than one sensor's waveforms can provide noise averaging as well as directional sensitivity. Impulsive signals also have the advantage of having a sharp rise time which can be very useful for determination of arrival by threshold crossing or peak detection methods.

If the sensors 46 and source 44 are nearly collocated, then the sensors 46 immediately detect the emitted sounds. These sounds also propagate through the medium 18 and into the ground. The first echo sensed at the sensors 46 will be from the ground/container interface, assuming any discontinuities exist which result from density differences. Ideally, if there were no impedance mismatches resulting from density differences, then there would be no other returns unless there are objects buried under the ground. As the sound propagates through the ground and hits a buried object, the sound will reflect back toward the container. Various sensors 46 in the container will detect the same returned signal at various arrival times and signal strengths. When the geometry of the sensors 46 is precisely known, these arrival times can be used to determine the arrival direction and distance from the sensors. Secondary reflections can be from other features of the buried object, such as by recessed surfaces or the bottom of the mine.

Modifications to the impinging waveform can result from internal voids, non-homogeneous materials, or thin-structure resonance. Time-difference-of-arrival (TDOA) techniques are well know for determining wavefront arrival directions. Delay is the two-way path length divided by the velocity of the wave. These techniques have been used in synthetic aperture radar and sonar applications.

If the sensor were being used to inspect the thickness or composition of a road, for example, ensuing echoes could result from the bottom surface of the road, as well as from the subsurface material bottom (such as gravel or sand). These echoes from each material result from discontinuities in acoustic impedance at the material boundaries, and the time of returns, when compared to the timing of the originating wave, determine the thickness of each layer of materials. This is based on the speed of sound in the media. Gating of return pulses can eliminate certain reflections from surfaces known not to be buried objects or the surface of the inspection area. These pulses could result from the other surfaces of the roller structure. Gating can also be used to remove the return from the surface of the ground and only look for object below the surface.

Additional applications of the invention include the detection of buried cables, pipes, ordnance, tunnels, sewer lines, lost objects, voids, material defects, inside walls or floors, or other conduits. The invention could be used to inspect the internal organs and tissues within a human or animal. Land, air, and sea vehicles, either unmanned or manned, can pull or push the invention over the area to be inspected. The invention could be attached to a dolphin or other animal to inspect the hull of a ship, for example.

Other applications for the invention include the inspection of walls and floors for joists, rebar, pipes, tunnels, and wires. The invention would also be useful for archeological uses, geological exploration and excavation and treasure finding. It has useful applicability for surf zone detection of mines in the regions of underwater approach, in the surf, on the beaches, and inland. The container can be built into shoes/attachment, similar to the known foam pads used to walk on minefields. Rolling the sensor over an animate body for active or passive acoustic imagery and sonic interpretation can also use the array. The farming industry can use such a device for locating rocks or inspecting buried crops. When used in conjunction with pipe or conduit inspection, passively listening for turbulence/flow and actively pinging for image formulation or measurements can provide invaluable data. Such a sensor or array can be built into tires of vehicles to inspect road surface, or used for the non-destructive evaluation of pipes, tanks, planes, or other structures: roller deforms to shape.

Figure 9:
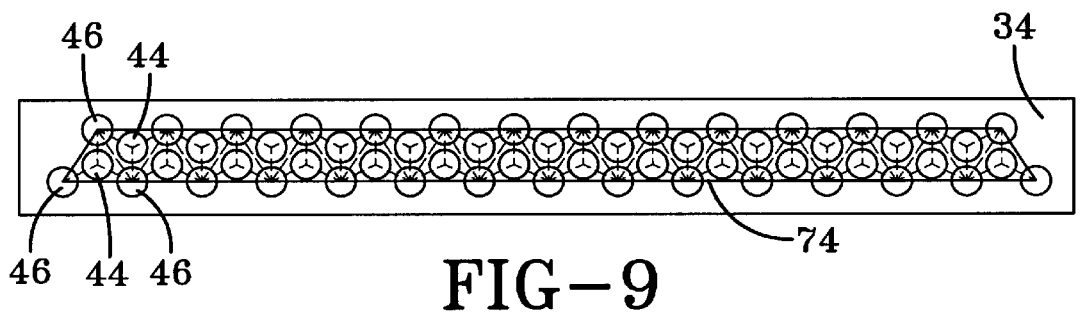
FIG. 9 schematically shows a typical array layout with multiple sensors in triangular patterns and sound sources embedded at the centers of each triad.

One or more sensors 46, preferably an array of sensors, can be used to better detect the arrival direction of returning signals. For example, FIG. 8 schematically shows a triad 70 of sensors 46 with a sound source 44 in the middle. The centers of the sensors 46 are located on the endpoints of an equilateral triangle and the center of the source 44 is located at the center of the equilateral triangle. The triad 70 can determine both azimuth and declination of the returning waves by using the time differences of arrival at each sensor 46. The formulas outlined by Arthur R. Hercz in "Fundamentals of Sound-Ranging" clearly describe the method of calculating the arrival direction and elevation based on wavefront propagation timing acquired from each sensor. These formulas are geometrically based, and rely on the relative separation of sensors in the wavefront propagation direction and the sound speed in the medium of mechanical wave propagation. These formulae are know to those practicing the art of sound localization, and will not be discussed in further detail. FIG. 9 schematically shows a typical array layout with multiple sensors 46 in triangular patterns and sound sources 44 embedded at the centers of each triad.

As an example of three-dimensional localization with a triad of sensors 46, consider a ground-propagating wave at the surface that hits the triad of sensors resting on the same surface. The time differences resulting from the propagation speed and sensor separation would exactly match the anticipated propagation distances of the triad's planar geometry (i.e. delay equals sensor separation distance divided by the propagation velocity in that media). If reflections from a buried object originated deep within the medium, the time of propagation between sensors would be less than the maximum delays associated with waves traveling within the same plane of the sensors. This reduction in propagation times, which indicate that the array has a smaller projected area resulting from the "Cosine(theta)" effect, indicates that the target is below the plane of sensors, and the angle can be predicted by geometric relationships derived from the wavefront timing. These relationships provide measures of azimuth and elevation relative to the midpoint of the triad of sensors. Other triads of sensors, formed by various combinations of other nearby sensors within the array, can formulate similar solutions to the same originating signal. With known positions of various local triads of sensors, a more accurate location of the wave origin can be achieved by calculating the intersection of numerous lines of bearing (both azimuth and declination). Limiting the field of view or regard to immediately below the array or just forward of the array will simplify computational aspects of array processing for target location.

It is the combination of these numerous estimates, as all possible combinations of sensors is calculated, which provide data for object visualization and physical property determination. As the array of sensors moves over the inspection area, recalculation of wavefront origination (at the mine) from new reference locations will provide additional data that better locates buried objects based on different view angles and ranges. The phase-delayed combination of sensor signals can provide signal strengths of sounds emanating from numerous buried targets, or various reflective surfaces of a single target.

Another method of sensor comparison is to calculate the transfer function of adjacent sensors to determine spectral variances in wave transmission and reflectivity at a particular location. Both phase and amplitude comparisons provide specific differences in frequency or phase which directly relate to the buried object depth, size, density, orientation, and mass. An average "background noise" can be calculated by averaging the spectrum from several sensors at one or more locations when known to be inspecting an area without any buried target. This background can then be subtracted from subsequent measurements that contain a similar background and may or may not contain a target. Subtracting out an average background will make detection of objects easier by enhancing differences from the average background.

Various combinations of acoustic sensors 46 can create a pair of stereo signals that can be relayed to the user through binaural headphones. Because the user's brain is accustomed to processing subtle differences in timing, phase, amplitude, and frequency content, his brain can contribute significant processing to the localization, detection, and understanding of objects detected. The virtual "left to right separation distance" should be scaled for the sound speed of the particular media so that the perceived separation between left and right signals are similar to the intra-aural timing of the users head. Similar intra-aural time differences permit use of spatial localization skills developed through years of normal sound interpretation through the user's unaided ears.

The shape of the underground object may be determined by mental visualization of amplitudes at edges from numerous passes. Accelerometers, or other geolocation sensors such as GPS, can be used to track the exact location of the sensors 46, and store the information to create a map of data collected. Also, orientation of the array of sensors 46 can be changed by rotation. Head mounted displays or tactile feedback in a headset or a handle offers clues for frequency content that may be present outside of the range of human hearing (infrasonic and ultrasonic). Pulse train modifications resulting from the phased combination of numerous sensors 46 and compared to an originating (reference) waveform can be relayed to the user through headsets as is or processed with filtering or frequency shifting for better auditory display. Variations to the amplitude and phase of the pulse trains will manifest themselves audibly when presented binaurally.

Broadband data from one or more sensors 46 can be presented "as is" to maximize user understanding of both sets of reflected energy, and how both sets are modified as a function of noise presence. An ambient (airborne) sensor 46 can be used as a noise-canceling reference to help eliminate unwanted airborne signals and enhance target-related sounds. One processing method would be to perform a transfer function between reference and left sensors and between the reference and right sensors, then do inverse FFTs on the two transfer function results and present these two time domain signals to the left and right headset speakers respectively. This is an adaptive method, since the transfer function will change as a result of ambient noise changes detected by both the reference sensor and the left and right detection sensors. The reference sensor should be relatively far from the ground impulses, so as not to include the impulses in the reference waveform used for the noise canceling. As an alternative to the FFT domain noise cancellation described above, simple differential amplifiers can be used with the reference signal being split and differenced in hardware with the left and right sensor detection channels. "Noise and signal" minus "signal" will produce only "signal". Cardioid or directional sensors can further reduce the environmental noise effects. These and other common noise canceling methods can be applied to various combinations of the liquid-coupled sensors 46.

Another method of sensor comparison is to merely look at current spectral or temporal energy in any one sensor as compared to the others. When the sensor is over a subsurface object, the reflections from an acoustic or seismic source will be higher at the sensor than when the sensor is monitoring an area without a buried object. These RMS or frequency measures can be plotted as a function of sensor location and traverse position. When an object is passed over, a visual indication of its presence will become evident in the amplitude or density graph. Applying this device for route survey purposes would enable the determination if mines have been placed after the initial survey was done by comparing the current findings with that of previous runs (this assumes the baseline was known to be without mine/mine-like targets).

The invention can also be used as an acoustic "sound probe", comprising a sound source 44 and two sensors 46 separated by a known distance, which when coupled to the ground will investigate soil sound conduction for site-specific calibration. This will help define for that particular soil optimized waveform parameters such as pulse width, bandwidth, or signal strength, as well as geometrical issues such as angle of incidence, sensor separation, or movement rate. All of these parameters can be varied to optimize performance. Data from this combined sensor configuration will provide indications of the soil's SNR, transmission, density, porosity, water content, boundary reflection, soil type, and natural clutter (stone, roots, etc.). Probe data will validate the presence and variations of multiple acoustic and seismic wave propagation velocities traveling between the granular particles as well as those waves that propagate through the bulk medium (See Tittmann and Tavossi, "Acoustic Detection Potential of Underground Non-Metallic Objects," Penn State University, ARL Battlefield Acoustic Symposium, September 1997). Information derived from this measurement may be useful to farmers or builders to ascertain the global stability of the ground, drainage potential, soil composition, in-situ density measurement, and other parameters.

Figure 10A:
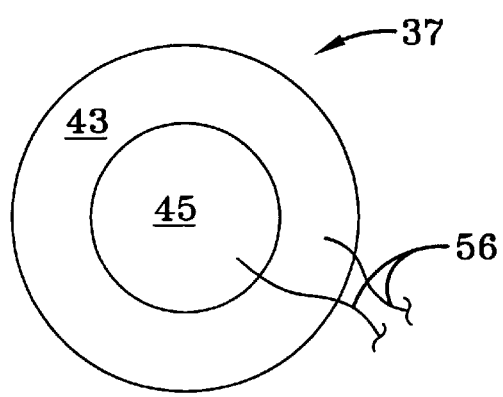
FIG. 10(A) is a top view of an exemplary sensor and FIG. 10(B) is a side view of the sensor of FIG. 10(A).
Figure 10B:
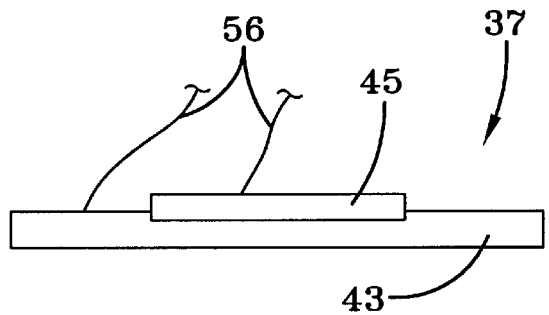

FIG. 10(A) shows a top view of an exemplary acoustic sensor for use in the invention. FIG. 10(B) is a side view of the sensor of FIG. 10(A). FIGS. 10(A) and (B) show a piezoelectric element 37 in the form of a disk. The element 37 comprises a ceramic disk 45 mounted on a metal disk 43. Wires 56 are connected to the ceramic disk 45 and the metal disk 43. Piezoelectric elements are available from MuRata Ltd., MuRata Part No. 7BB-20-6A0. It should be apparent to those of skill in the art that the piezoelectric element 37 may be used as either an acoustic sensor or an acoustic source. When used as an acoustic sensor, the piezoelectric element 37 transduces impinging acoustic signals to electrical signals that are routed through the wires 56. When used as an acoustic source, the piezoelectric element 37 receives electrical signals via the wires 56 and transduces the electric signals to acoustic signals that are emitted from the element.

Figure 11:
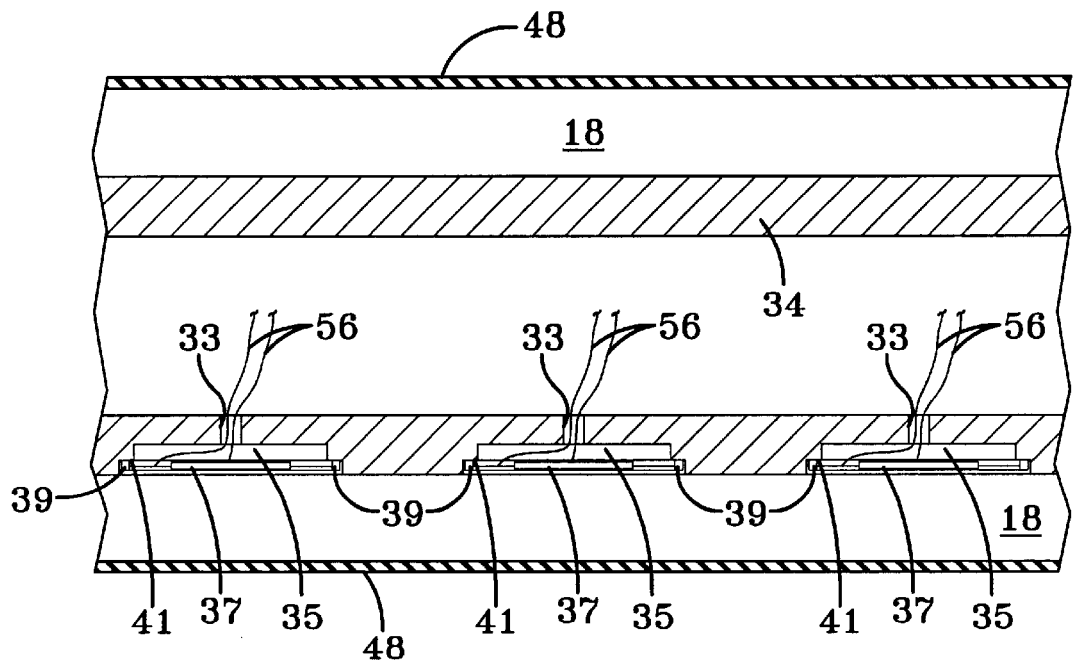
FIG. 11 schematically shows an exemplary method of mounting sensors.

FIG. 11 schematically shows an exemplary method of mounting the piezoelectric element 37. A bladder 48 containing a medium 18 surrounds a hollow shaft 34. Piezoelectric element 37 is suspended in front of a cavity 35 in the shaft 34. Adhesive sealer 39 is applied to only the outermost edge the element 37 so that the element 37 adheres to ledge 41. Air is preferred within cavity 35. The adhesive sealer 39 holds the element 37 in place and prevents medium 18 from getting behind the element 37 and shorting it out. Passageways 33 in shaft 34 permit wires 56 to pass into the center of the shaft where all the wires can be routed. Although not shown, a sealer should also be used where the wires 56 exit the passageways 33 to prevent moisture from entering cavities 35, as well as to prevent any acoustic path for sounds to travel through the center of shaft 34. Medium 18 contacts the metal surface of each element 37. A protective and insulating cover for the elements 37 may be used to help preserve and electrically isolate them. Care should be taken to only use material for the cover that has good acoustic transmission properties, such as a thin coat of an RTV (room temperature vulcanizing) material, or thin and flexible rubber or plastic.

Figure 12:
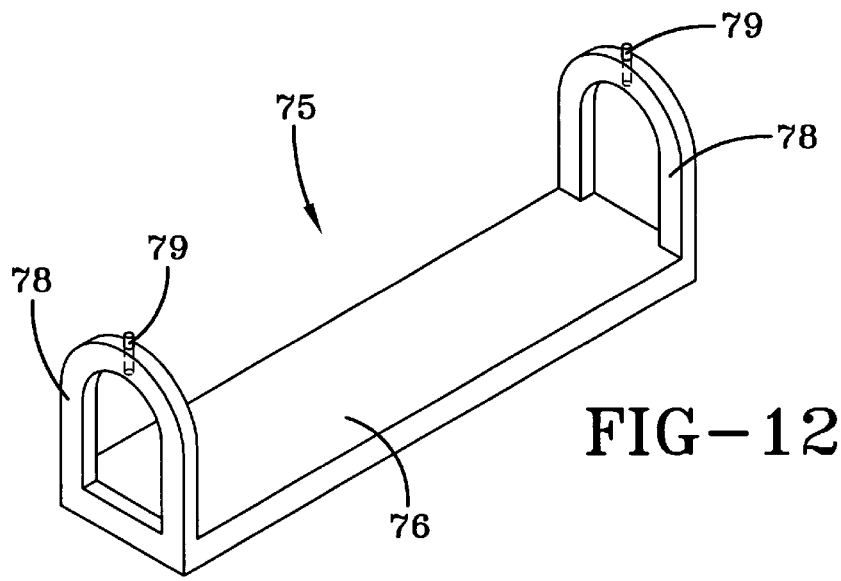
FIG. 12 is a schematic perspective view of a calibration bar.

FIG. 12 is a schematic perspective view of a calibration bar 75 for a roller, such as roller 32 in FIG. 4. The calibration bar 75 calibrates the sources 44 and sensors 46 to compensate for variations in sound speed, individual sensor phase or amplitude variations, as well as inter-channel differences in phase or amplitude. The calibration bar 75 comprises a flat, reflective surface 76 suspended from two brackets 78. When in use, the brackets 78 suspend the reflective surface 76 beneath the sensors and sources 46, 44. The brackets 78 fit around the hose clamps 52 shown in FIG. 4. Set screws 79 hold the calibration bar 75 in place. When not in use, the bar 75 is rotated 180 degrees and stowed above the roller 32. The set screws 79 hold bar 75 in the stowed position. The calibration bar 75 may be made of metal or plastic with a smooth surface, so that it is a strong acoustic reflector. Preferably, the bar 75 is made of aluminum.

Because the reflective surface 76 is flat and at a known and constant distance from the sensors and sources 46, 44, the reflections off the surface 76 are identical for similar sensor and source geometries. With a known and constant distance between the sensors and sources and the calibration bar 75, the round trip propagation time from the sensor or source to the bar 75 and back again is directly related to the density of the medium 18. The density of the medium 18 varies with temperature and water content. The reflections from the bar 75 are used to adjust coefficients such as amplitude or phase variations to optimize sensor and source performance.

Another method of calibration is to measure the velocity of sound in the ground by injecting a sound into the ground 13 (See FIGS. 2 and 3) at one end of the roller 32 and monitoring the time of propagation to one or more sensors 46 within the roller of known geometry. An emitted sound will travel both in the medium 18 and in the ground 13, thereby allowing a direct and simultaneous method of measuring both the medium's and the ground's sound velocities, as well as the individual sensors responses to the traveling waves.

Figure 13:
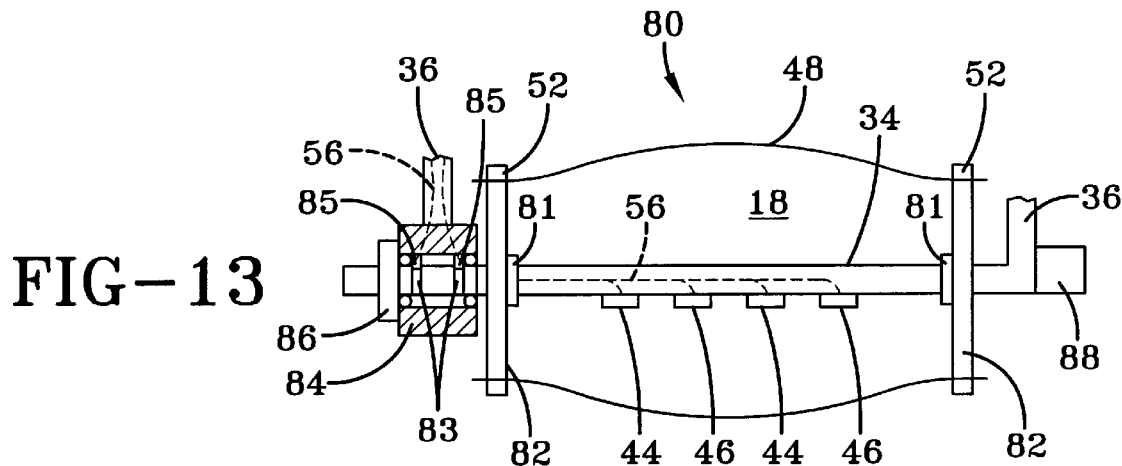
FIG. 13 is a schematic, cutaway view of another embodiment of a roller.

FIG. 13 is a schematic, cutaway view of an embodiment of another roller 80 of the invention. Roller 80 includes a bladder 48 with medium 18 contained therein. Bladder 48 is attached to flanges 82 by, for example, hose clamps 52. A hollow shaft 34 has one or more sources 44 and sensors 46 mounted thereon. Flanges 82 are tightly attached to shaft 34 and sealed on the inside of bladder 48 by seals 81.

Wires 56 from sensor(s) and source(s) arc routed through the hollow interior of shaft 34 to the left side of roller 80, as shown in FIG. 13. Wires 56 terminate at conductive bands 83 on shaft 34. One end of spring loaded contacts 85 contacts conductive bands 83 and the other end of the contacts 85 are connected to additional wiring 56. A roller bearing 84 fits around shaft 34 and maintains spring loaded contacts 85 in place. A retaining flange 86 is tightly fitted to shaft 34 and maintains roller bearing 84 in place.

Handle 36 (FIG. 2) is attached to the exterior surface of bearing 84 and shaft 34 at the left side of FIG. 13. Wires 56 pass through holes in the exterior surface of bearing 34 into the interior of handle 36. Acoustic source and sensor electronics 23, 25 and output device 38 are mounted on handle 36 or carried by the operator.

As the operator pushes on the upper part of the handle 36, the bladder 48, shaft 34 and flanges 82 all rotate as the apparatus moves forward. The orientation of the source(s) 44 and sensor(s) 46 rotates as the shaft 34 rotates. Although the preferred method of use is a hand-held device that is pushed by a person, the same device could be attached to a vehicle or robot and moved with the platform. Larger length rollers can be used to clear roads or large sections of beaches. Inspection rollers can be used in yards, construction zones, or other areas where underground visualization is necessary.

In FIG. 13, only the left side of the roller 80 is shown having the conductive bands 83 on the shaft 34, the spring loaded contacts 85, the roller bearing 84 and the retaining flange 86. However, if more conductive bands are necessary to transmit signals from the sensors 46 and sources 44, the right side of roller 80 may be constructed like the left side. It should be understood that the embodiment of FIG. 13 may also be modified to include a rear wheel assembly 47 as shown in FIG. 3, sensors and sources located outside of the roller 80 as shown in FIG. 6, an additional front roller 80 as shown in FIG. 7 and an array of sensors and sources as shown in FIGS. 8 and 9.

Figure 14:
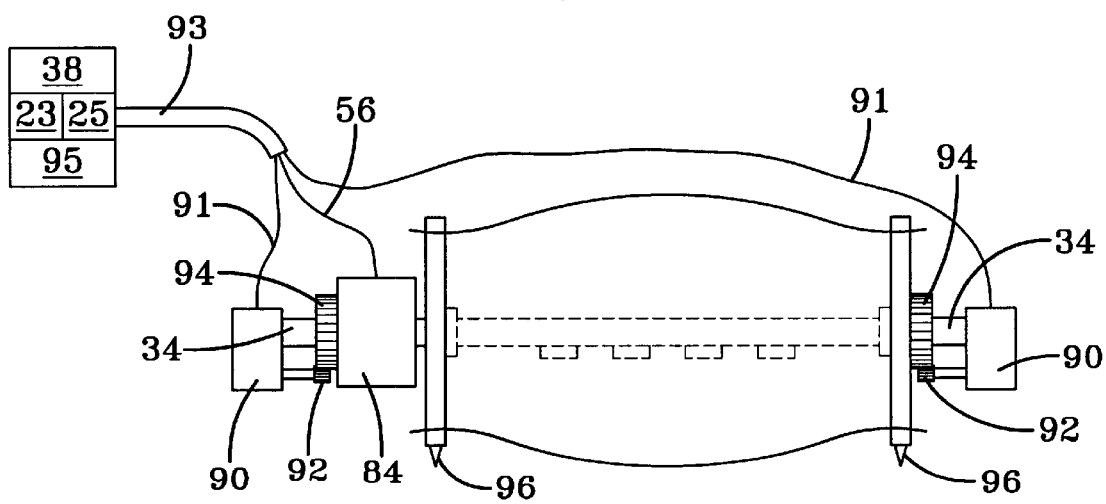
FIG. 14 is a schematic, cutaway view of a modification of the embodiment of FIG. 13.

FIG. 14 schematically shows an embodiment of the roller 80 in which the roller is self-propelled. Each end of the shaft 34 has a high torque electric motor 90 mounted thereon. Motors 90 drive gears 92 which mesh with gear teeth on retaining flanges 94. Rotation of retaining flanges 94 causes rotation and movement of the roller 80. Motors 90 are remotely controlled through wiring 91 which is combined with wiring 56 in a flexible conduit 93. At the end of conduit 93 are motor controllers 95, acoustic source and sensor electronics 23, 25 and output device 38. Wiring 91 and 56 may be replaced by RF, IR, acoustic or other types of transmitters and receivers.

By remotely varying the motor speed ratios and spin directions, the roller 80 can advance, retreat, or turn. Thus, the operator may remain at a safe distance while using the self-propelled roller to clear and mark a path. Marking the pathway the roller 80 has traversed can be accomplished by mechanical means such as two protrusions 96 on flanges 82 that scrape the ground. Other means for marking, such as depositing markers like paint or emissive chemicals that are viewable by image intensifiers or infrared imagers are also possible. Larger rollers, attached to the front of vehicles or construction equipment, can be pushed in front of the vehicle to investigate buried objects in roads or terrain. Another embodiment is a roller that is pulled by a helicopter or unmanned aerial vehicle.

Constant awareness of position and orientation can be used to make a map of objects detected. A combination of GPS (global positioning system), inertial (accelerometers and angular rate) sensors, movement encoders (such as rotary on shaft or wheels), image translation, or other known methods of position and orientation measurement can locate the mines relative to a known reference. The known reference could be GPS coordinates, a digital map location, or relative to the start of roller movement. Precisely locating the objects with differential GPS permits transmitting the locations of detected objects to other interested parties to aid them in detection and remediation. In FIG. 13, a GPS receiver 88 is attached to shaft 34 or handle 36. The GPS output is part of the output device 38.

Motion sensors such as Hall-effect transducers or encoders on the shaft 34 of the roller 80 will give indications of how much the roller has moved. This motion data can be used to calculate the exact position of the sensor during a measurement. A composite image of the numerous measurements can be created to visualize a buried object, and position that object in geographic space. The output device 38 may comprise a computer display to visualize objects detected in the inspection area. The data processor 42 may use data evaluation methods such as target strength, resonances, Doppler effects, phase, time-delay-of-arrival, wavenumber, cross-correlation, and dispersion effects. Audio outputs resulting from the selection of one or more outputs to monitor, or combinations of various sensors can provide auditory clues as to the presence of buried objects. The human ears and brain are excellent signal processors and may interpret and understand audio clues that detection algorithms may miss. The operator's mind can learn with continuous operation, and may augment automated detection algorithms.

Figure 15:
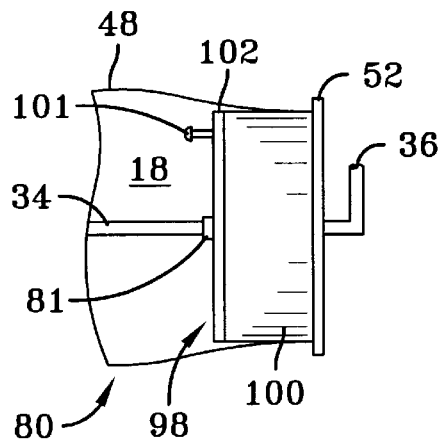
FIG. 15 is a schematic view of a modification of the right hand side of the roller of FIG. 13.
Figure 16:
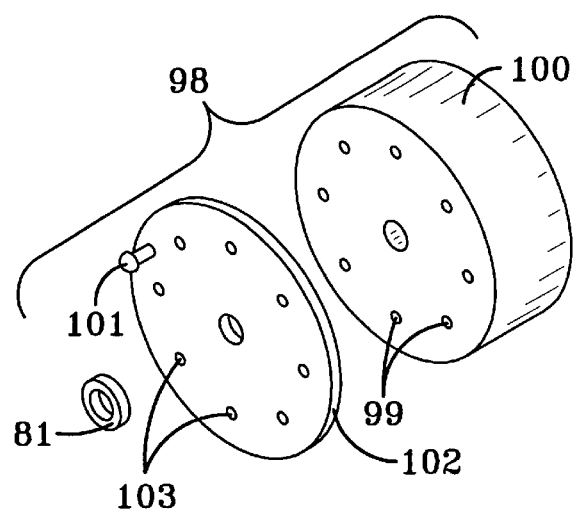
FIG. 16 is an exploded view of the collection chamber assembly of FIG. 15.

FIG. 15 is a schematic view of a modification of the right hand side of the roller 80 of FIG. 13. The roller 80 of FIG. 13 is modified by replacing the right hand side flange 82 with a collection chamber assembly 98. FIG. 16 is an exploded view of the collection chamber assembly 98. Assembly 98 includes chamber 100 with openings 99, open/close plate 102 with openings 103 and an actuator knob 101 attached to the open/close plate 102.

As in the embodiment of FIG. 13, the bladder 48 is attached to chamber 100 by hose clamp 52. Shaft 34 penetrates collection chamber assembly 98 and is attached to handle 36. Chamber 100 is tightly fitted to shaft 34 so that chamber 100 rotates with shaft 34. Openings 99 allow medium 18 into chamber 100. Open/close plate 102 is friction fitted to shaft 34 so that it rotates therewith. However, plate 102 may be rotated on shaft 34 by grasping actuator knob 101. Although actuator knob 101 is located inside of bladder 48, knob 101 may be grasped by simply pushing on the bladder 48 and grasping knob 101 through the flexible material of bladder 48. Open/close plate 102 fits against chamber 100. Seal 81 seals the collection chamber assembly from medium 18. The chamber 100 is open to medium 18 when the openings 99 in chamber 100 are aligned with the openings 103 in plate 102. Conversely, chamber 100 is closed to medium 18 when the openings 99 in chamber 100 are covered by plate 102. The position of plate 102 is changed by rotating plate 102 via knob 101.

The purpose of collection chamber assembly 98 is to vary the density of the medium 18. For example, medium 18 may comprise liquid and particulate matter, as in the case of drilling mud. To reduce the density of medium 18, roller 80 is put in a vertical position with collection chamber assembly 98 at the bottom. The plate 102 is placed in the open position to permit dense particulate to settle into chamber 100 where it is effectively removed from the remaining medium 18. Thus, the average density of the medium 18 in the sensing area is decreased. The size of chamber 100 determines the maximum percentage change in density of medium 18. A few percent change of total particulate is sufficient to account for changes in moisture or for soil type variations. When the chamber 100 is in the bottom position, dense particulate settles and is sealed into the chamber. On the other hand, if chamber 100 is in the top position and the plate 102 is opened, particulate contained in chamber 100 is allowed to pass into medium 18, thereby increasing the effective density of medium 18.

Even when roller 80 is in a horizontal position, gravity creates a density gradient in the roller. Other liquids or slurries, for example, caster oil, electrolytes, etc. may be combined to provide imiscible or gradually varying density gradients. Numerous imiscible liquids provide multi-layer matching that gravity helps to orient vertically, with the most dense at the bottom and the least dense at the top.

Figure 17B:
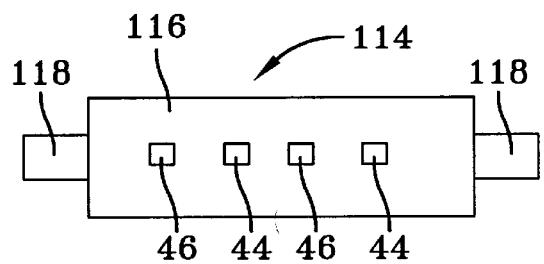
FIG. 17(A) is a perspective view of a shaft for use in a roller and FIG. 17(B) is a bottom view of the shaft of FIG. 17(A).
Figure 17A:
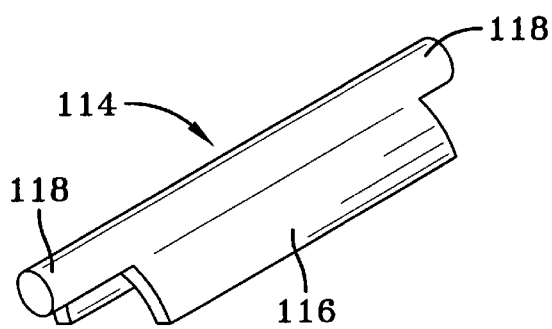

FIG. 17(A) is a schematic perspective view of another shaft 114 for use with the rollers of the invention. FIG. 17(B) is a bottom view of the shaft 114 of FIG. 17(A). Shaft 114 includes a shroud portion 1 16 and a bearing portion 118. One or more sensors 46 and, if desired, one or more sources 44 are mounted on shaft 114. The sensors 46 and sources 44 are mounted on shaft 114 in the manner shown in FIG. 11, for example. Shroud portion 116 may define a circular or parabolic arc with the sensors and sources mounted at the apex thereof. Shroud portion 116 improves emission of signals and reception of signals by virtue of its shape and directivity. Shaft 114 may be mounted in a roller such as shown in FIG. 4. The bearing portion 118 of shaft 114 functions the same as the end portions of shaft 34 in FIG. 4.

Figure 17C:
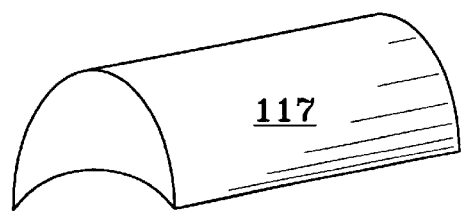
FIG. 17(C) is a perspective view of an acoustic absorber for use with the shaft of FIG. 17(A).

FIG. 17(C) shows an absorber 117 for use with shaft 114. The absorber 117 is attached to the top of shaft 114 with, for example, an adhesive. Absorber 117 is made of an anechoic or absorptive material. Absorber 117 enhances performance by minimizing confusing reflections that may be traveling within the shaft 114 or within medium 18 at its top surface. Absorber 117 also provides a dimensional stability aspect, so that the top surface of the roller material can only sag to a minimal level.

Figure 18:
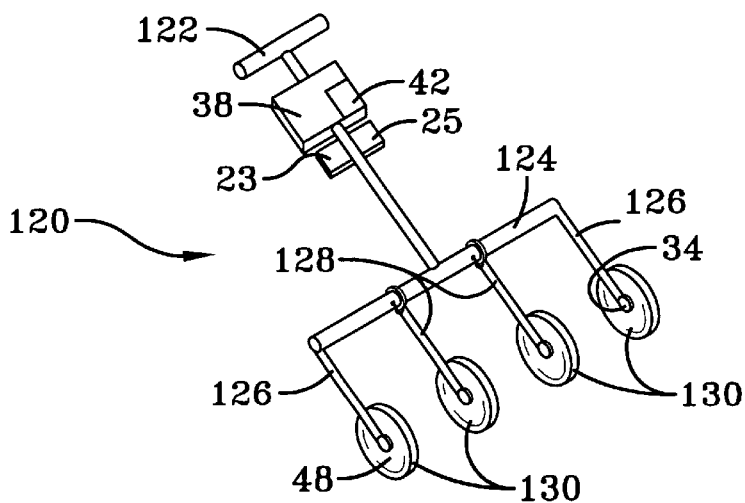
FIG. 18 is a schematic perspective view of another embodiment of the apparatus of the invention.

Sensor arrays do not need to be rigid and conform to terrain, especially if beamforming is not necessary (exact location of sensor not required for precise time difference of arrival). FIG. 18 is a schematic perspective view of another embodiment of an apparatus 120 of the invention. Apparatus 120 comprises a plurality of rollers 130. The two end rollers 130 are connected to a transverse member 124 by end arms 126. The end arms 126 are fixed with respect to the transverse member 124. The interior rollers 130 are connected to the transverse member 124 by rocker arms 128. The rocker arms 128 may rotate with respect to the transverse member 124. The transverse member 124 is connected to a handle 122 for pushing the apparatus 120. Wiring from the sensor(s) 46 and/or source(s) 44 in the rollers 130 is routed through the interiors of the end arms 126 and rocker arms 128 to the transverse member 124 and then to the handle 122. Mounted on the handle 122 are the sensor and source electronics 25, 23 and the output device 38 which may include a data processor 42. Alternatively, the sensor and source electronics 25, 23 and the output device 38 may be carried by the operator of the apparatus 120.

The rocker arms 128 rotatably attached to the transverse member 124 support the interior rollers 130 while allowing them to adapt to varying contours of the ground immediately below each roller. Because the rollers 130 are not acoustically coupled to each other, acoustic measurements from adjacent rollers 130 are isolated. With a single continuous roller, sounds can travel within the ground and the roller, which may confuse detection or localization algorithms. The plurality of independent rollers 130 prevents above ground coupling between sensor locations. Each roller 130 moves independently over the terrain, with acoustic coupling occurring at the point where the roller 130 deforms with the ground contour. Apparatus 120 is especially useful when absolute location of the sensors is not required. If desired, positional sensors may be added to keep track of the relative positional relationships of the sensors for more precise beamforming.

Rollers 130 may be constructed similarly to roller 32 shown in FIG. 4. Each roller 130 includes a shaft 34 with one or more sensors 46 and/or sources 44 mounted thereon. Bladder material 48 contains a medium 18. Bearings 50, hose clamps 52 and seals 54 are included at the ends of shaft 34. Unlike roller 32 of FIG. 4, where shaft 34 is connected to handle 36, the shafts 34 of the rollers 130 are connected on one end only to either an end arm 126 or a rocker arm 128. As the apparatus 120 is pushed forward, the bladder 48 and medium 18 in the rollers 130 rotates while the shafts 34 with sensors and sources mounted thereon do not rotate.

Figure 19A:
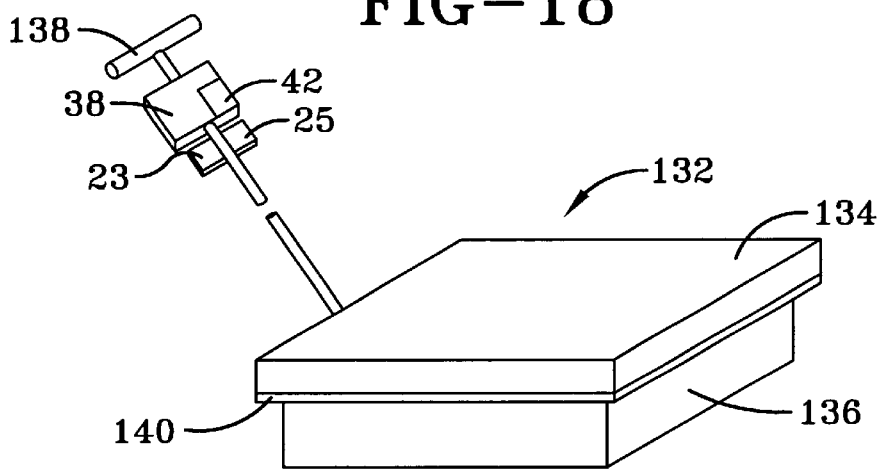
FIG. 19(A) is a schematic perspective view of another embodiment of the apparatus of the invention.
Figure 19B:
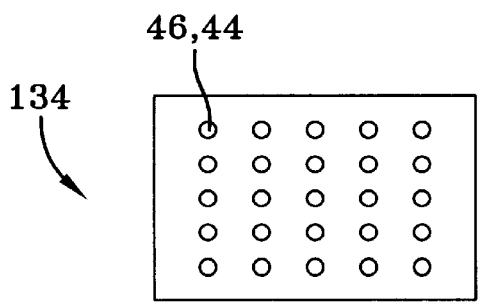
FIG. 19(B) is a bottom view of the top plate of the embodiment of FIG. 19(A) and FIG. 19(C) is a bottom view of a flange of the embodiment of FIG. 19(A).
Figure 19C:
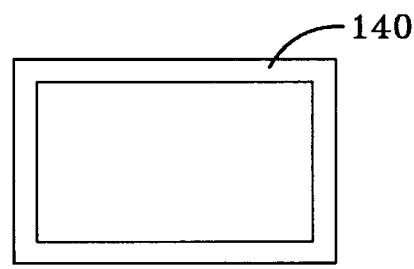

The principle of the present invention is also useful without the "roller" concept. FIGS. 19(A)–19(C) schematically show an apparatus 132 including a planar array of acoustic sensors 46 that may be placed over a target area and used to study the target area in great detail while stationary. The apparatus 132 includes a generally rectangular shaped container 136 made of acoustically transparent material like that of bladder 48. The container 136 contains medium 18. Container 136 is closed on top by a rigid hollow plate 134 made of plastic or metal. As shown in FIG. 19(B), a planar array of sensors 46 and, if needed, sources 44 are mounted in the bottom of plate 134. Handle 138 is attached to top plate 134.

FIG. 19(C) shows a flange 140 used to hold and seal the container 136 to the top plate 134. Flange 140 may be made of the same material as plate 134. The top edges of container 136 are sealed between flange 140 and plate 134. Flange 140 is connected to plate 134 by fasteners, for example, bolts. Sealant material may be used if needed to provide a liquid tight seal around the periphery of flange 140. The acoustic sensor and source electronics 25, 23 may be contained in the plate 134, on the handle 138 or be carried by the operator of the apparatus.

Figure 19D:
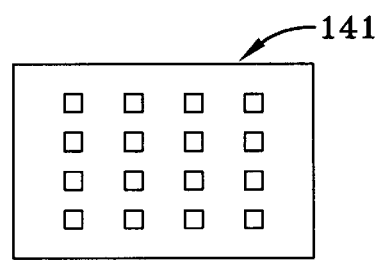
FIG. 19(D) is a bottom view of another flange.

FIG. 19(D) shows another flange 141 used to hold and seal the container 136 to the top plate 134. Flange 140 may be made of the same material as plate 134. The top edges of container 136 are sealed between flange 141 and plate 134. Flange 141 is connected to plate 134 by fasteners, for example, bolts. Sealant material may be used if needed to provide a liquid tight seal between plate 134 and flange 141. Flange 141 differs from flange 140 in that it is formed in a grid-like configuration thereby creating a plurality of subcontainers out of container 136. Each subcontainer contains medium 18 and is fluidly sealed from adjacent subcontainers. The grids in flange 141 are configured such that each subcontainer is disposed beneath a sensor 46 or source 44 mounted in the plate 134.

The medium 18 and container 136 will deform to the contours of the ground, deforming with respect to the stationary array of sensors 46. Therefore, the relative positions of individual sensors 46 remains constant, with the medium 18 and container 136 material continuously varying with the changing ground geometry. Slight rotation or translation of the apparatus 132 provides a new perspective on the buried objects. Sound sources 44 embedded within the plate 134 or external to it provide stimulus waveforms for the array of sensors 46 to interpret. Indication of a buried target can be relayed to the user by a variety of output devices 38, such as visual displays, graphics on a computer screen, or audio indicators either broadcast through the air or through headphones.

Figure 20A:
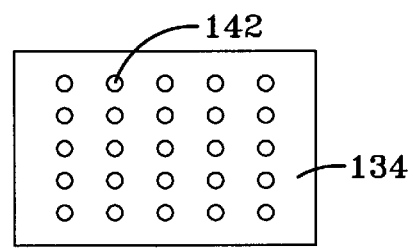
FIG. 20(A) is a top view of the top plate of the embodiment of FIG. 19(A) and FIG. 20(B) is a schematic view of a sensor channel.
Figure 20B:
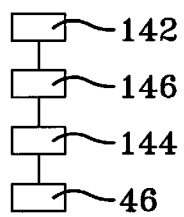

Rather than a large number of data acquisition channels and data processing to produce an output display, a simplified analog/discrete component system shown in FIGS. 20(A) and (B) allows visualization of the acoustic data. Individual sensors 46 with preamplifier 144, filter 146, and a visual indicator 142, such as an LED or LCD, comprise a single channel. The sensors 46 are mounted in the bottom of plate 134. The preamplifier and filter are disposed inside the plate 134. A visual indicator (LED or LCD) 142 for each sensor 46 is mounted on top of plate 134. A plurality of noise sources 44 may also be embedded within the plate 134 for active pinging. Noise sources on the shoes of the person operating the apparatus 132 can also create mechanical waves that will propagate under the container 136.

Because each sensor 46 is connected to a visual indicator 142, pressure fluctuations from mechanical waves traveling under the container 136 are visible on the indicators 142. The amplitude of the light or indicator 142 is directly related to the amplitude of the acoustic waves detected. Obviously, phase and frequency content can also be used to modulate the visual indicators 142. Both amplitude and color can be modified. When the container 136 is placed over a suspected target, active pinging produces detailed imagery of the buried object. Time difference of arrival triangulation methods may be used to create a three dimensional map of the target location. Three dimensional visualization techniques, such as holograms or volume density plots, can provide visual indications of target location and orientation.

The array of visual indicators 142 on the top surface of the plate 134 provides a 2-dimensional representation of sensor amplitudes by varying the color or amplitude of the individual indicators 142 corresponding to each sensor 46 below. Additional visual indicators 142 (light sources) between the sensor locations increase resolution of the detected image. The average of the surrounding sensor indicator values can be applied to the indicator located between the sensor indicators resulting in a two dimensional interpolation to increase the density of light indicators for better visualization. Successive interpolations can further improve resolution. Such interpolation may better help object edge visualization.

For example, assume plate 134 contains a square planar array of 100 acoustic sensors 46 and 100 indicators 142 on the top surface of the plate 134. The preamplifiers 144 and filters 146 contained within plate 134 amplify the acoustic signals and create light indications of signal strength. The electronics are very similar to a volume indicator light, and are well known to one skilled in electrical design. When the container 136 is centered over a round object, high acoustic energy measured at the sensors 46 closest to the buried object create the highest amplitude light signal or the brightest color in a specified color density plot.

Temporal response of the light indicators 142 should be fast enough to correspond to the maximum frequency detectable by the human eye. Low pass filtering of individual channels limits the response of the amplifier channels and removes the higher frequency fluctuations that the human eye cannot respond to. This limit would be at least ten Hertz. Higher frequency response could also be allowed to pass through and allow the human eye and brain to comprehend as much as possible. Higher frequency responses can be stored by the electronics, and replayed at a slower time base so that the human eye can comprehend the faster variations of the light indicator fluctuations. The visual indicators 142 could also be located on the handle 138 of the apparatus 132. Alternatively, the signals may be transferred to a heads-up display or remote monitor inside a nearby vehicle. To improve the visual resolution of the indicators 142, more indicators 142 can be placed between all the other indicators, and the measurements controlling the intensity of the interstitial indicators can result from an average of two or more of the nearest sensor indicators 142. This would provide a blending of the data points, and a better resolution for viewing the shape and edges of an object.

Figure 25A:
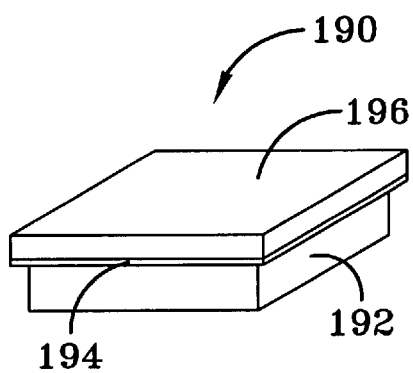
FIGS. 25(A)–(E) schematically show another embodiment of the invention.
Figure 25B:
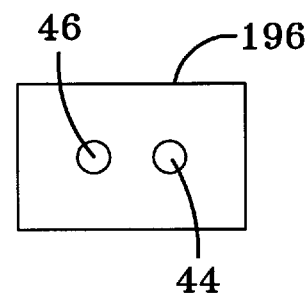
Figure 25C:
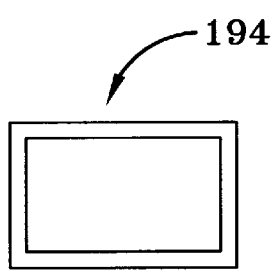

FIGS. 25(A)–(E) schematically show another embodiment of the invention. FIG. 25(A) shows an apparatus 190 very much like apparatus 132 in FIG. 19(A). Apparatus 190 includes a generally rectangular shaped container 192 made of acoustically transparent material like that of bladder 48. The container 192 contains medium 18. Container 192 is closed on top by a rigid hollow plate 196 made of plastic or metal. As shown in FIG. 25(B), a single sensor 46 and, if needed, a source 44 is mounted in the bottom of plate 196. FIG. 25(C) shows a flange 194 used to hold and seal the container 192 to the top plate 196. Flange 194 may be made of the same material as plate 196.

Figure 25D:
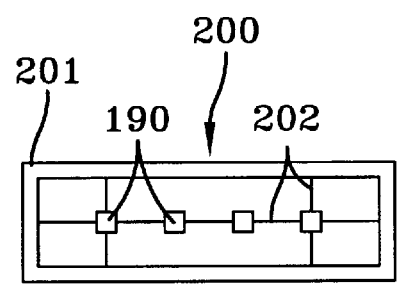
Figure 25E:
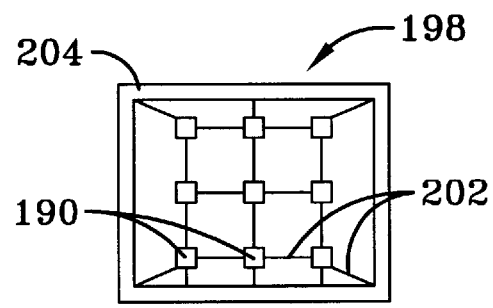

As shown in FIG. 25(D), apparatus 200 comprises a plurality of the apparatuses 190 mounted inside a frame 201. The apparatuses 190 comprise a linear array. The apparatuses 190 are attached to frame 201 with elastic members 202. A handle such as handle 138 in FIG. 19(A) may be attached to frame 201 and, if desired, acoustic source and sensor electronics 23, 25 and output device 38 may be mounted on the handle. FIG. 25(E) shows apparatus 198 which is a planar array of apparatuses 190 mounted to frame 204 with elastic members 202. The elastic members 202 may be, for example, springs or rubber members. Each single sensor apparatus 190 is able to seek its own position and deformation based on the local ground contours.

Figure 21:
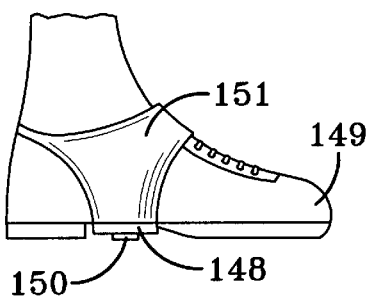
FIG. 21 is a side view of a sound source mounted on a shoe.

FIG. 21 shows an acoustic source 148 attached to a person's shoe 149. The source 148 is located in the space between the front of the heel and the ball of the foot. The source 148 is supported by a fabric web 151 that fits over the shoe 149. The shoe source 148 introduces vibrations/noise into the soil as the person wearing the shoe 149 walks. Using one of the embodiments of the invention described above permits detection of acoustic reflections or resonances resulting from the noise created by the shoe source 149.

Sound and vibration sources located on the shoes of the user provide additional energy to the underground object for resonance and reflected energy detection. A push button pressure switch 150 in the shoe source 149 activates the sound source. Varying the location of the feet and the emission sequences provides diversity in wavefront propagation and the resulting reflected energy. The push button pressure sensor 150 turns on and off the sound/vibration source 148. The operator may want one or both shoe sources 148 on at a time to maximize energy at the underground object. Varying foot placement will change reflection effects. Impulse, CW, and white/broadband noise sources can be selected. Placement of the feet can be varied to enhance edge detection of buried objects. Sound sources could also be contained in an external device like a backpack. The sound source may be, for example, an impulsive, high amplitude source that channels the sound to the ground via an acoustic conduit or freefield propagation. Transfer functions and correlation techniques provide frequency and timing differences to returning signals.

Figure 22:
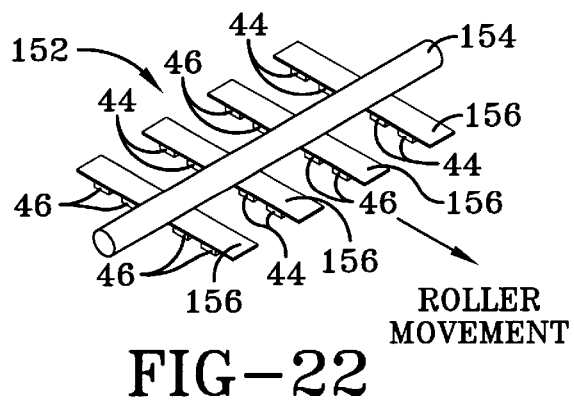
FIG. 22 is a schematic perspective view of a shaft with a planar array of sources and sensors.

A planar array of sources and sensors, such as shown in FIGS. 19(A)–(C), may also be used in a roller configuration. The roller is constructed like the roller 32 in FIG. 4, except that the portion of the shaft 34 inside the roller 32 is modified. FIG. 22 shows a modified shaft 152 to provide a planar array in a roller. Shaft 152 includes a transverse portion 154 and at least one longitudinal portion 156. Sensors 46 and sources 44 are attached to the bottom of the longitudinal portions 156. Sensor and source wiring is routed through the interior of the longitudinal portions 156 to the interior of the transverse portion 154 and then to the handle (not shown). The planar array provides detailed spatial information, and the process of moving the roller while acquiring data provides the dynamic, multi-perspective data to include Doppler effects.

The application of side-scan sonar or synthetic aperture radar (or acoustic) theory directly applies to a roller used with the shaft 152 of FIG. 22. A line array of sensors whose axis is parallel to the direction of travel is the identical situation of a side-scan sonar being towed through the water. In the case of side-scan sonar, echoes or sound returns from water discontinuities, underwater targets, and the floor of the water basin, are similar to the returns which would be detected by the present invention detecting buried objects within different materials with different sound speeds.

Figure 23:
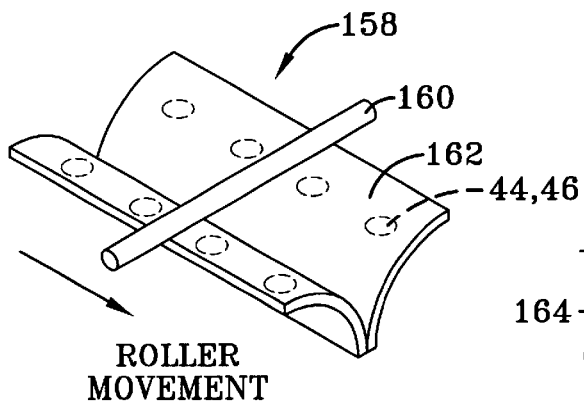
FIG. 23 is a schematic perspective view of a shaft with a planar array and a baffle.

Various combinations of directional microphones, acoustic baffles, and focusing apertures can provide additional directional sensitivity. FIG. 23 shows a modification of the shaft 152 of FIG. 22. Shaft 158 includes a transverse portion 160 and a longitudinal focusing baffle 162. Sensors 46 and/or sources 44 are mounted on the bottom of longitudinal focusing baffle 162. Directional sensitivities are created by the longitudinal focusing baffle 162. The sensors 46 and sources 44 travel within the roller in a direction parallel to the focusing baffle 162. This concept is very similar to the towed sonar arrays used for side-scan sonar. The longitudinal focusing baffle 162 produces directional sensitivities perpendicular to the baffle, and the sensors 46 monitor the signal strength and timing from targets in the beam's maximum sensitivity direction.

Figure 24:
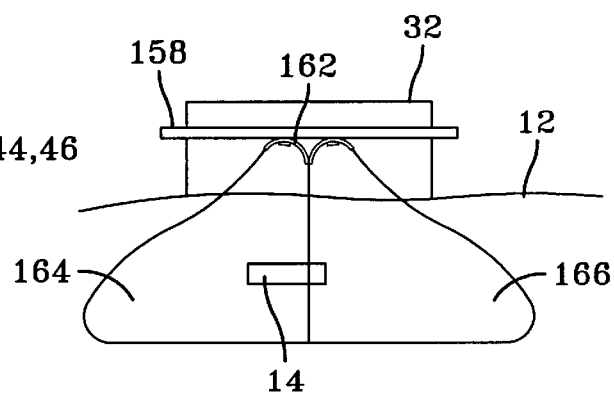
FIG. 24 schematically shows signal fields created using a baffle.

FIG. 24 schematically shows the signal fields created by using the longitudinal focusing baffle 162. Signal field 164 is created by sources on the left side of baffle 162 and signal field 166 is created by sources on the right side of baffle 162. The target 14 under the ground surface 12 lies mostly in the left side field 164. The simultaneous combination of several or all sensors and sources in each array will produce a directional array with maximum sensitivity broadside (perpendicular) to the baffle 162. Directional sensors and acoustic lenses can also be used to produce a preferential direction.

The combination of at least two sensor waveforms with a time (phase) delay will create a focused directional response for preferential reception of returning signals. When the delay is zero, the summed signal combination creates a focused beam perpendicular to the line of sensors. Adding timing delays can have the effect of steering a beam in a preferred direction. In the case of a linear array of sensors, beams from adjacent and overlapping combinations of sensors provide the look forward and look downward capability to detect objects in front of and below the array.

Figure 26:
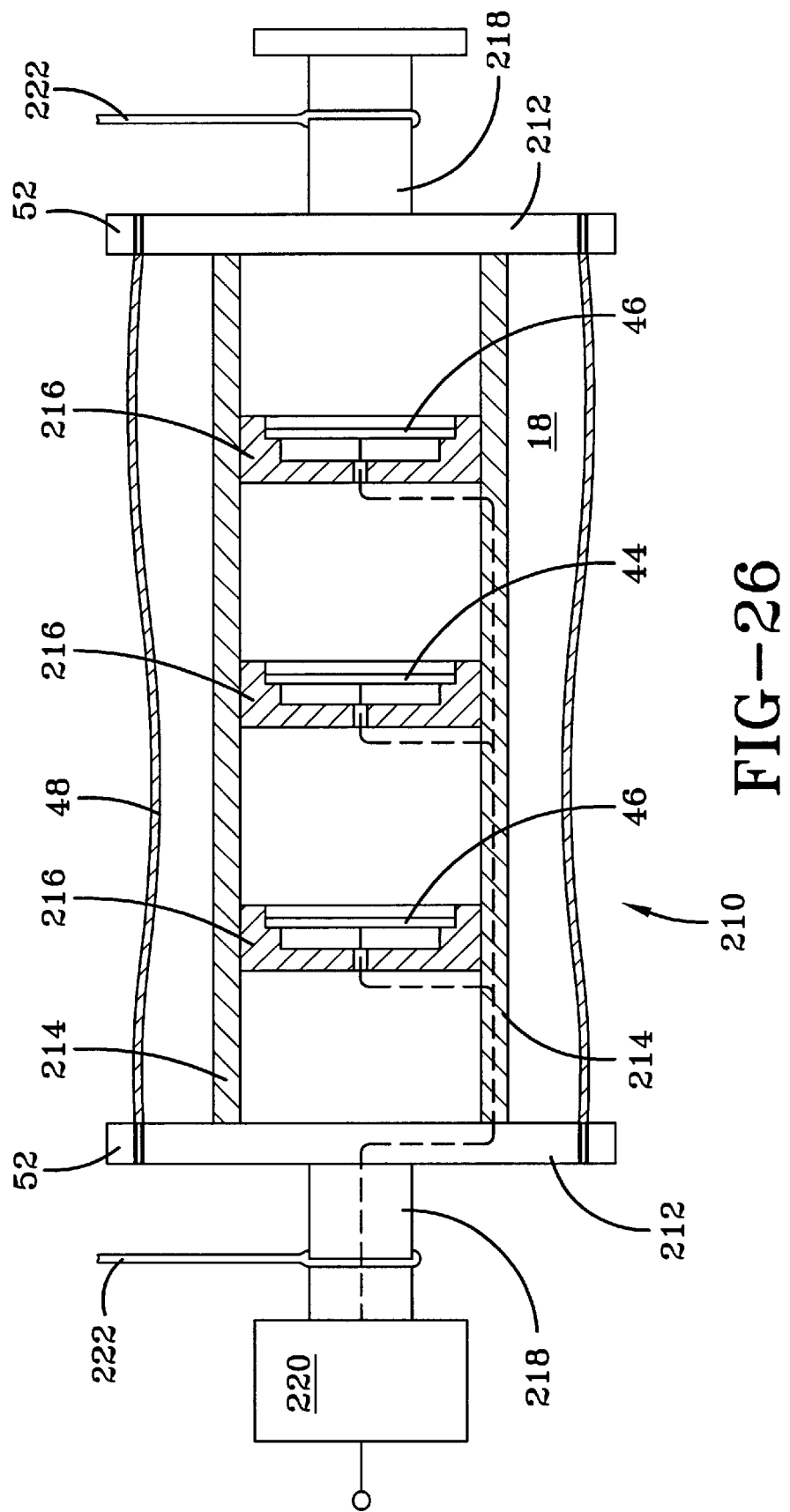
FIG. 26 schematically shows another embodiment of the invention.

FIG. 26 schematically shows another embodiment of a generally cylindrical roller type apparatus 210. Apparatus 210 includes a bladder 48 filled with a medium 18. The bladder 48 is attached to two rigid or semi-rigid end caps 212 with hose clamps 52. A support structure 214 for sensors 46 and/or sources 44 is mounted inside the bladder 48 and attached to the end caps 212. In FIG. 26, the support structure is two rods. Other types of support structures may be used, such as wires, a mesh tube or any other minimally acoustically obstructive structure. Mounting plates 216 for sensors or sources are connected to the support structure 214. At least one sensor 46 is disposed in a mounting plate 216. One or more sources 44 may also be disposed in additional mounting plates 216.

On the outside of the two end caps 212 are shaft hubs 218. On one of the shaft hubs 218 a transmitter 220 is attached for transmitting data to a remote location. The transmitter may include circuitry such as a battery, preamplifier, filter, analog to digital converter and digital signal processor. Attached to the shaft hubs 218 are cables 222. The cables 222 may be pulled by a human or attached to a machine, such as an unmanned aerial vehicle, a helicopter or a robot. Alternatively, rather than cables 222, a handle (not shown) may be attached to the shaft hubs 218. In the event a handle is used, then suitable bushings or the like would be used to attach the handle to the shaft hubs 218.

Wiring from the sensors and/or sources is routed through the mounting plates 216 to the inside of a hollow member of the support structure 214 through the end cap 212 and the hollow shaft hub 218 to the transmitter 220. Alternatively, the wiring may be simply routed from each mounting plate 216 through the medium 18 in the central area of the support structure 214 to the end cap 212. In the apparatus 210, the entire apparatus rotates except, of course, the cables or handle. The sensors 46 and/or sources 44 are mounted in a substantially omni-directional orientation so that rotation of the roller does not affect sensor directivity response.

While the invention has been described with reference to certain preferred embodiments, numerous changes, alterations and modifications to the described embodiments are possible without departing from the spirit and scope of the invention as defined in the appended claims, and equivalents thereof.

What is claimed is:

1. An apparatus for detecting an underground object, comprising:

a roller container having a generally cylindrical shape being in contact with a ground surface, wherein at least a portion of said roller container that contacts the ground is substantially acoustically transparent and made of a substantially flexible material of one of rubber, polyethylene, polyvinylchloride, vinyl and a plastic material, such that the portion of the roller container that contacts the ground surface substantially conforms to a contour of the ground surface;

a medium of at least one liquid and one gel disposed in the roller container;

a shaft that passes through the roller container;

a plurality of acoustic sensors for detecting acoustic noise disposed in the medium in the roller container and arranged in triads so that at least one of the acoustic sensors is mounted on the shaft;

a plurality of acoustic sources that emit acoustic noise symmetrically located at a midpoint of each sensor triad such that at least one of the acoustic sources is mounted on the shaft; and an output device connected to the plurality of acoustic sensors.

2. An apparatus for detecting an underground object, comprising:

a roller container having a generally cylindrical shape being in contact with a ground surface, wherein at least a portion of said roller container that contacts the ground is substantially acoustically transparent and made of a substantially flexible material of one of rubber, polyethylene, polyvinylchloride, vinyl and a plastic material, such that the portion of the roller container that contacts the ground surface substantially conforms to a contour of the ground surface;

a medium of at least one liquid and one gel disposed in the roller container;

a shaft that passes through the roller container;

a handle attached to the shaft for moving the roller across the ground surface;

a rear wheel assembly attached to the handle, for decreasing loading of the roller on the ground surface;

at least one acoustic sensor disposed in the medium in the roller container, for detecting acoustic noise roller wherein the at least one acoustic sensor is mounted on the shaft;

at least one acoustic source that emits acoustic noise wherein the at least one acoustic source is mounted on the shaft; and an output device connected to the plurality of acoustic sensors.

3. An apparatus for detecting an underground object, comprising:

a roller container having a generally cylindrical shape being in contact with a ground surface, wherein at least a portion of said roller container that contacts the ground is substantially acoustically transparent and made of a substantially flexible material of one of rubber, polyethylene, polyvinylchloride, vinyl and a plastic material, such that the portion of the roller container that contacts the ground surface substantially conforms to a contour of the ground surface;

a medium of at least one liquid and one gel disposed in the roller container;

a shaft that passes through the roller container;

at least one acoustic sensor disposed in the medium in the roller container, for detecting acoustic noise roller wherein the at least one acoustic sensor is mounted on the shaft;

at least one acoustic sensor disposed outside of the roller;

a frame attached to the shaft of the roller for supporting the at least one acoustic sensor disposed outside of the roller; and an output device connected to the acoustic sensor.

4. An apparatus for detecting an underground object, comprising:

a roller container having a generally cylindrical shape being in contact with a ground surface, wherein at least a portion of said roller container that contacts the ground is substantially acoustically transparent and made of a substantially flexible material of one of rubber, polyethylene, polyvinylchloride, vinyl and a plastic material, such that the portion of the roller container that contacts the ground surface substantially conforms to a contour of the ground surface;

a medium of at least one liquid and one gel disposed in the roller container;

a shaft that passes through the roller container;

at least one acoustic sensor disposed in the medium in the roller container, for detecting acoustic noise roller wherein the at least one acoustic sensor is mounted on the shaft;

a second roller container located in front of the roller container and a frame attached to the shaft of the roller container for supporting the second roller; and an output device connected to the acoustic sensor.

5. An apparatus for detecting an underground object, comprising:

a roller container having a generally cylindrical shape being in contact with a ground surface, wherein at least a portion of said roller container that contacts the ground is substantially acoustically transparent and made of a substantially flexible material of one of rubber, polyethylene, polyvinylchloride, vinyl and a plastic material, such that the portion of the roller container that contacts the ground surface substantially conforms to a contour of the ground surface;

a medium of at least one liquid and one gel disposed in the roller container;

a shaft that passes through the roller container;

at least one acoustic sensor disposed in the medium in the roller container, for detecting acoustic noise roller wherein the at least one acoustic sensor is mounted on the shaft;

a collection chamber assembly mounted on the shaft inside the roller container at one end thereof, the collection chamber assembly comprising a chamber with openings formed therein for collecting and releasing higher density medium; and an output device connected an output device connected to the acoustic sensor.

6. The apparatus of claim 5, wherein the collection chamber assembly further comprises an open/close plate with openings formed therein for selectively opening and closing the openings formed in the chamber.

7. An apparatus for detecting an underground object, comprising:

a roller container having a generally cylindrical shape being in contact with a ground surface, wherein at least a portion of said roller container that contacts the ground is substantially acoustically transparent and made of a substantially flexible material of one of rubber, polyethylene, polyvinylchloride, vinyl and a plastic material, such that the portion of the roller container that contacts the ground surface substantially conforms to a contour of the ground surface;

a medium of at least one liquid and one gel disposed in the roller container;

at least one acoustic sensor disposed in the medium in the roller container, for detecting acoustic noise roller;

at least one acoustic source that emits acoustic noise;

a shaft that passes through the roller container wherein the shaft includes a bearing portion and a shroud portion, the at least one acoustic sensor and the at least one acoustic source being mounted on the shroud portion; and an output device connected to the acoustic sensor.

8. The apparatus of claim 7, further comprising an acoustic absorber mounted on a top of the shroud portion.

9. An apparatus for detecting an underground object, comprising:

a container having a rigid top plate, said container being in contact with a ground surface wherein at least a portion of said container is substantially acoustically transparent;

a medium of at least one liquid and one gel disposed in the container;

at least one acoustic sensor for detecting acoustic noise mounted on the bottom of the rigid top plate and disposed in the medium in the container; and an output device connected to the acoustic sensor.

10. The apparatus of claim 9, further comprising a plurality of acoustic sensors mounted on the bottom of the rigid top plate.

11. The apparatus of claim 10, further comprising a handle attached to the rigid top plate.

12. The apparatus of claim 10, further comprising a plurality of preamplifiers connected to the plurality of acoustic sensors, respectively, at least one of a plurality of filters, a plurality of means for modifying a signal and a plurality of means for processing a signal connected to the plurality of preamplifiers, respectively, and a plurality of visual indicators connected to the plurality of filters respectively.

13. The apparatus of claim 12, wherein the plurality of preamplifiers and the at least one of a plurality of filters, a plurality of means for modifying a signal and a plurality of means for processing a signal are disposed in an interior of the rigid top plate and the plurality of visual indicators are mounted on a top of the rigid top plate.

14. The apparatus of claim 1, further comprising a plurality of roller containers, the plurality of roller containers comprising two end roller container and at least one interior roller container a transverse member; two end arms connected at one end to an end roller container and at the other end rigidly connected to the transverse member; at least one rocker arm connected at one end to the at least one interior roller containers and at the other end rotatably connected to the transverse member; and a handle connected to the transverse member.

15. The apparatus of claim 1, further comprising a global positioning system attached to the apparatus.

16. A method of detecting an underground object, comprising:

emitting acoustic noise toward the underground object using at least one acoustic source and receiving the acoustic noise from the underground object with at least one acoustic sensor immersed in a medium, the medium being disposed in a container in contact with a ground surface;

focusing the emitted acoustic noise using one of a shroud and a baffle.

converting the received acoustic noise to electrical signals; and using an output device, converting the electrical signals to a form that can be sensed by a human to determine if the underground object has been detected.

17. A method of detecting an underground object, comprising:

receiving at least one of acoustic noise emanating from and acoustic noise reflected from the underground object with at least one acoustic sensor immersed in a medium, the medium being disposed in a container in contact with a ground surface;

imparting directional sensitivity to the at least one acoustic sensor using one of a shroud and a baffle.

converting the received acoustic noise to electrical signals; using an output device, converting the electrical signals to a form that can be sensed by a human to determine if the underground object has been detected.

18. An apparatus for detecting an underground object, comprising:

a plurality of the following device:

a container in contact with a ground surface, wherein at least a portion of the container that contacts the ground surface is substantially acoustically transparent, and wherein the container comprises a rigid top plate;

a medium disposed in the container, wherein the medium is at least one of liquid and gel;

at least one acoustic sensor disposed in the medium in the container, for detecting acoustic noise, the at least one acoustic sensor comprising a single acoustic sensor mounted on a bottom of the rigid top plate;

an output device connected to the acoustic sensor:

a frame; and a plurality of elastic members for connecting the plurality of said devices to said frame and to each other.

19. The apparatus of claim 18, wherein the plurality of said devices comprise a linear array.

20. The apparatus of claim 18, wherein the plurality of said devices comprise a planar array.

21. The apparatus of claim 18, wherein at least one of the plurality of said devices includes an acoustic source.

* * * * *